United States Patent
Sleva et al.

(10) Patent No.: US 7,037,268 B1
(45) Date of Patent: May 2, 2006

(54) LOW PROFILE ACOUSTIC SENSOR ARRY AND SENSORS WITH PLEATED TRANSMISSION LINES AND RELATED METHODS

(75) Inventors: Michael Z. Sleva, Charlotte, NC (US); Allen Eberhardt, Raleigh, NC (US); Cal T. Swanson, Apex, NC (US); Richard Triolo, Raleigh, NC (US); Simon J. Lewandowski, Raleigh, NC (US)

(73) Assignee: MedAcoustics, Inc., Melbourne, FL (US)

( * ) Notice: Subject to any disclaimer, the term of this patent is extended or adjusted under 35 U.S.C. 154(b) by 0 days.

(21) Appl. No.: 09/914,682

(22) PCT Filed: Feb. 29, 2000

(86) PCT No.: PCT/US00/05124

§ 371 (c)(1),
(2), (4) Date: Feb. 12, 2002

(87) PCT Pub. No.: WO00/54897

PCT Pub. Date: Sep. 21, 2000

Related U.S. Application Data

(60) Provisional application No. 60/122,264, filed on Mar. 1, 1999, provisional application No. 60/132,041, filed on Apr. 30, 1999.

(51) Int. Cl.
*A61B 8/14* (2006.01)
(52) U.S. Cl. ............... 600/459; 600/437; 600/466; 73/662; 340/855.6
(58) Field of Classification Search ............... 600/437, 600/459, 466; 73/662; 340/855.6
See application file for complete search history.

(56) References Cited

U.S. PATENT DOCUMENTS

| | | | |
|---|---|---|---|
| 4,234,813 A | 11/1980 | Iguchi et al. | 310/366 |
| 4,308,870 A | 1/1982 | Arkans | 128/640 |
| 4,376,302 A | 3/1983 | Miller | 367/157 |

(Continued)

FOREIGN PATENT DOCUMENTS

EP 0420190 A2 4/1991

(Continued)

OTHER PUBLICATIONS

Akay et al., "Noninvasive acoustical detection of coronary artery disease using the adaptive line enhancer method," Medical & Biological Engineering & Computing, vol. 30, pp. 147-154 (March 1992).

(Continued)

*Primary Examiner*—Brian L. Casler
*Assistant Examiner*—William Jung
(74) *Attorney, Agent, or Firm*—Myers Bigel Sibley & Sajovec PA

(57) ABSTRACT

A low profile acoustic array (10) is configured to selectively respond to shear waves while rejecting compression wave energy in the frequency range of interest. One sensor array is configured as a linear strip with a frame segment having at least one longitudinally extending rail and a plurality of sensor elements (20) extending therefrom. These sensor elements have a resilient core and opposing PDVF outer layers configured with opposing polarities onto the core. The linear strip array also includes a pair of separate electrical signal transmission paths. The transmission lines can include a series of undulations formed thereon to help minimize undesired mechanical crossover between sensors. A carrier member can be configured to be detachably releasable carries the discrete sensors to maintain the positional alignment until they are secured to a patient.

58 Claims, 28 Drawing Sheets

U.S. PATENT DOCUMENTS

| | | | |
|---|---|---|---|
| 4,424,465 A | 1/1984 | Ohigashi et al. | 310/335 |
| 4,491,051 A | 1/1985 | Barcus | 84/1.16 |
| 4,549,551 A | 10/1985 | Dyck et al. | 128/689 |
| 4,586,514 A | 5/1986 | Schlager et al. | |
| 4,697,597 A | 10/1987 | Sanz et al. | 128/699 |
| 4,777,961 A | 10/1988 | Saltzman | 128/715 |
| 4,792,145 A | 12/1988 | Eisenberg et al. | 128/715 |
| 4,805,633 A | 2/1989 | Kotani et al. | 128/715 |
| 4,833,659 A | 5/1989 | Geil et al. | 367/155 |
| 4,862,361 A | 8/1989 | Gordon et al. | 364/413.06 |
| 4,905,706 A | 3/1990 | Duff et al. | 128/701 |
| 4,947,859 A | 8/1990 | Brewer et al. | 128/715 |
| 5,035,247 A | 7/1991 | Heimann | 128/715 |
| 5,036,857 A | 8/1991 | Semmlow et al. | 128/715 |
| 5,109,863 A | 5/1992 | Semmlow et al. | 128/715 |
| 5,164,627 A | 11/1992 | Popek | 310/313 B |
| 5,301,679 A | 4/1994 | Taylor | 128/773 |
| 5,337,752 A | 8/1994 | Reeves | 128/700 |
| 5,365,937 A | 11/1994 | Reeves et al. | 128/715 |
| 5,398,689 A | 3/1995 | Connor et al. | 128/662.03 |
| 5,595,188 A * | 1/1997 | Kassal | 600/586 |
| 5,598,845 A | 2/1997 | Chandraratna et al. | 128/662.03 |
| 5,638,823 A | 6/1997 | Akay et al. | 128/691 |
| 5,680,863 A | 10/1997 | Hossack et al. | 128/662.03 |
| 5,687,738 A | 11/1997 | Shapiro et al. | 128/715 |
| 5,704,365 A | 1/1998 | Albrecht et al. | 128/702 |
| 5,727,561 A | 3/1998 | Owsley | 128/691 |
| 5,795,299 A | 8/1998 | Eaton et al. | 600/459 |
| 5,807,268 A | 9/1998 | Reeves et al. | 600/528 |
| 5,807,271 A | 9/1998 | Tayebi et al. | 600/511 |
| 5,831,492 A * | 11/1998 | Solie | 333/193 |
| 5,853,005 A | 12/1998 | Scanlon | 128/662.03 |
| 5,885,222 A | 3/1999 | Kassal et al. | 600/528 |
| 5,913,829 A * | 6/1999 | Reeves et al. | 600/528 |
| 6,178,344 B1 * | 1/2001 | Hull et al. | 600/407 |
| 6,193,668 B1 | 2/2001 | Chassaing et al. | 600/481 |
| 6,243,599 B1 | 6/2001 | Van Horn | 600/407 |
| 6,261,237 B1 | 7/2001 | Swanson et al. | 600/527 |
| 6,278,890 B1 | 8/2001 | Chassaing et al. | 600/407 |
| 6,558,323 B1 * | 5/2003 | Wakabayashi et al. | 600/437 |

FOREIGN PATENT DOCUMENTS

| | | |
|---|---|---|
| EP | EP 0518508 A1 | 5/1992 |
| EP | EP A 0 528 279 | 2/1993 |
| EP | 0801927 A1 | 10/1997 |
| FR | FR A 2 507 424 | 12/1982 |
| JP | JP04126135 | 4/1992 |
| WO | WO92/08407 | 5/1992 |
| WO | WO94/30030 | 12/1994 |
| WO | WO 95/06525 | 3/1995 |
| WO | WO98/22786 | 5/1998 |

OTHER PUBLICATIONS

Akay et al., "Noninvasive Acoustical Detection of Coronary Artery Disease: A Comparataive Study of Signal Processing Methods," IEEE Transactions on Biomedical Engineering, vol. 40, No. 6, pp. 571-578 (June 1993).

Fraden, "Application of Piezo/Pyroelectric Films in Medical Transducers," Jour. of Clinical Eng., vol. 13, No. 3, pp. 133-138 (Mar.-Apr. 1988).

Nilsson et al., "A Combined Microphone for Simultaneous Recording of Pulse, Phono and Reference ECG," Electromedica, vol. 2, No. 76, pp. 64-68 (1976).

Wang et al., Modeling Sound Generation in Stenosed Coronary Arteries, IEEE Transactions on Biomedical Engineering, vol. 37, No. 11, pp. 1087-1094 (November 1990).

* cited by examiner

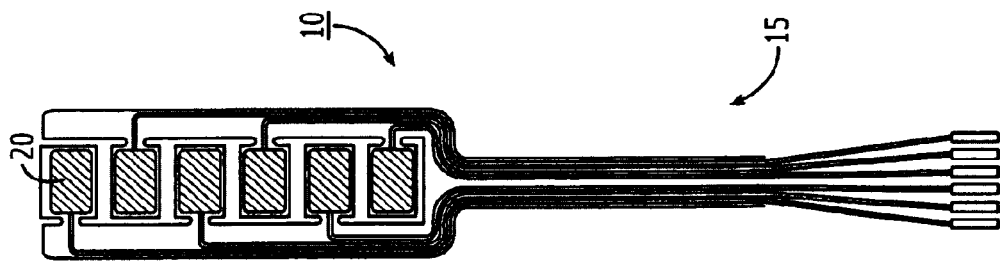
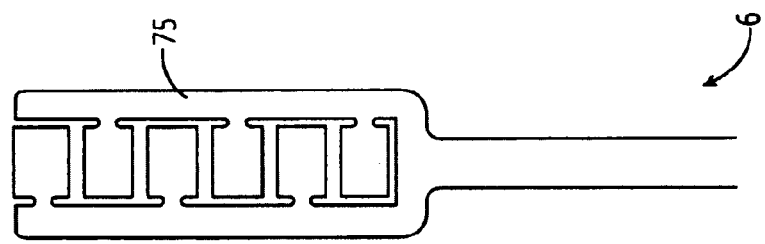
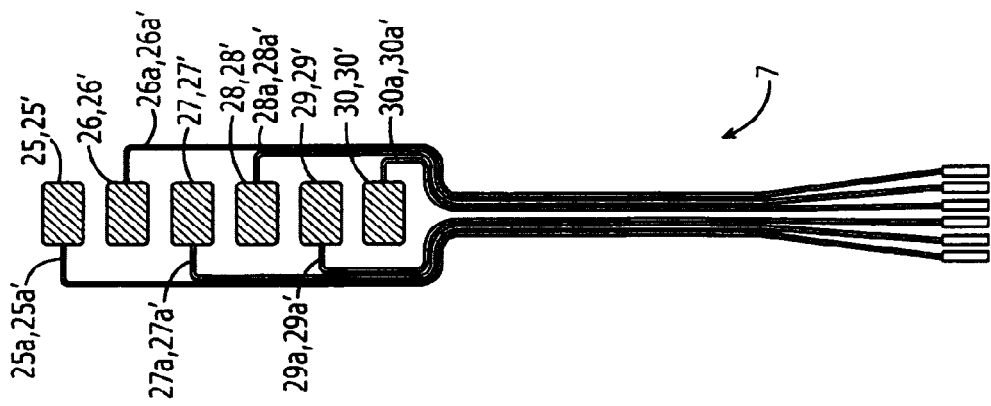
FIG. 1A

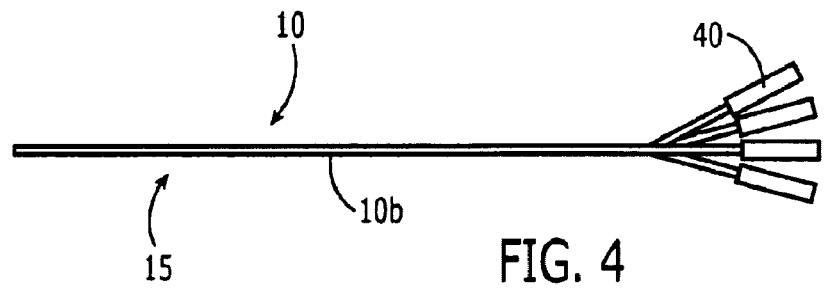
FIG. 4
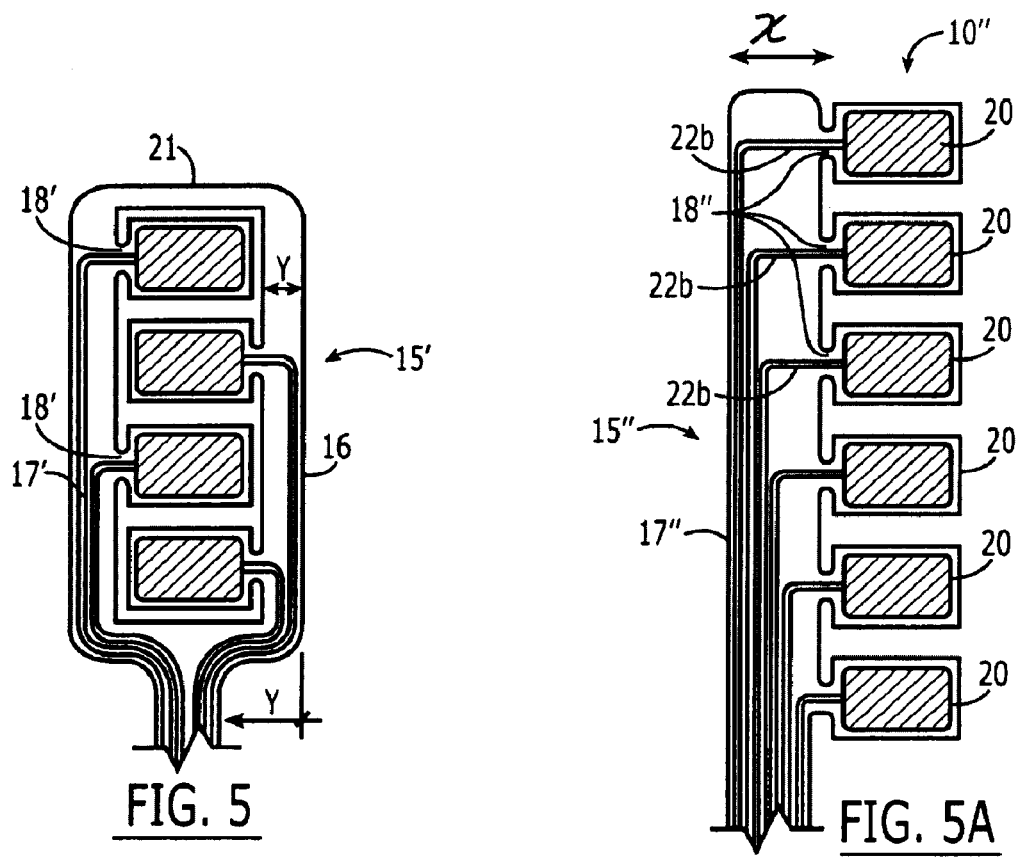
FIG. 5
FIG. 5A

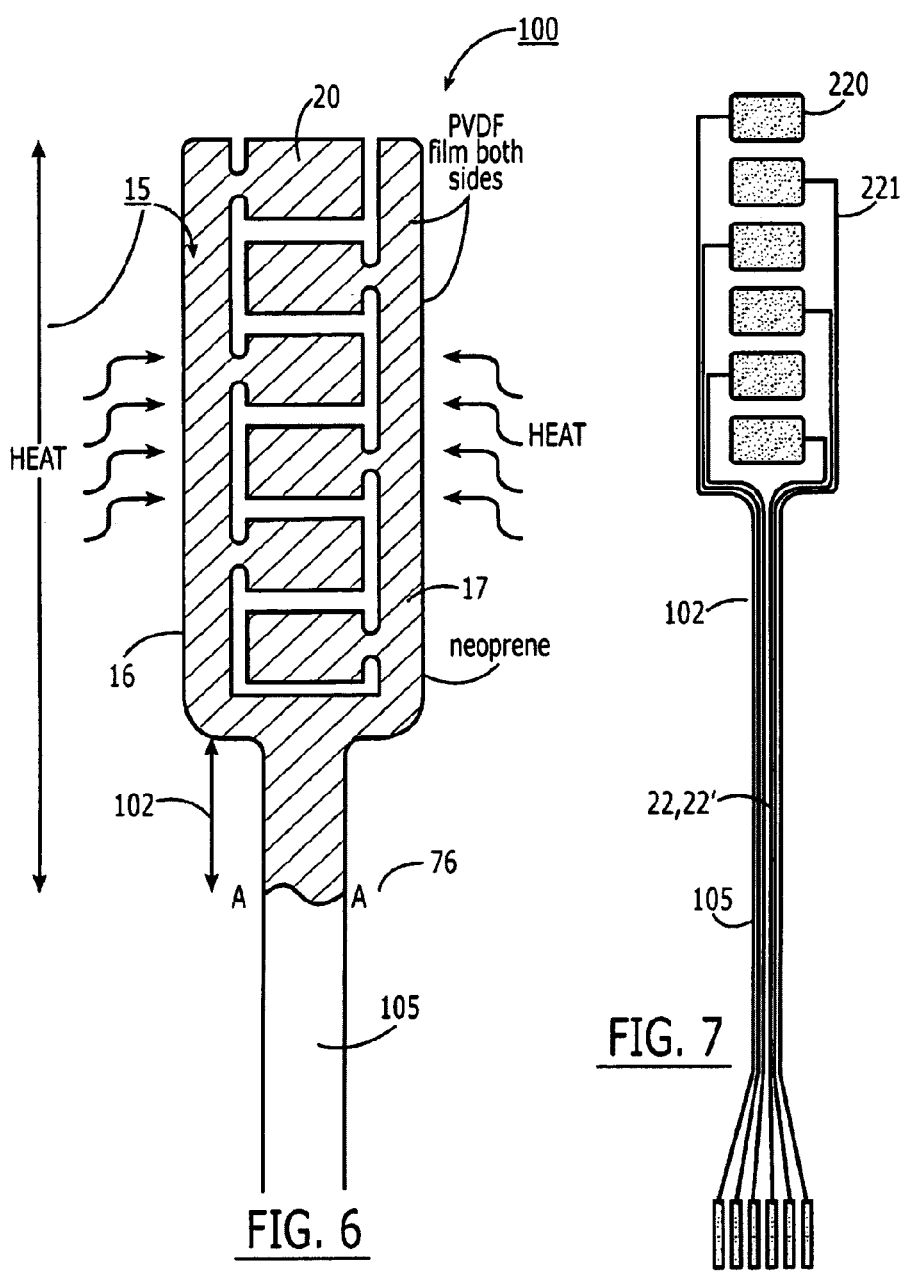

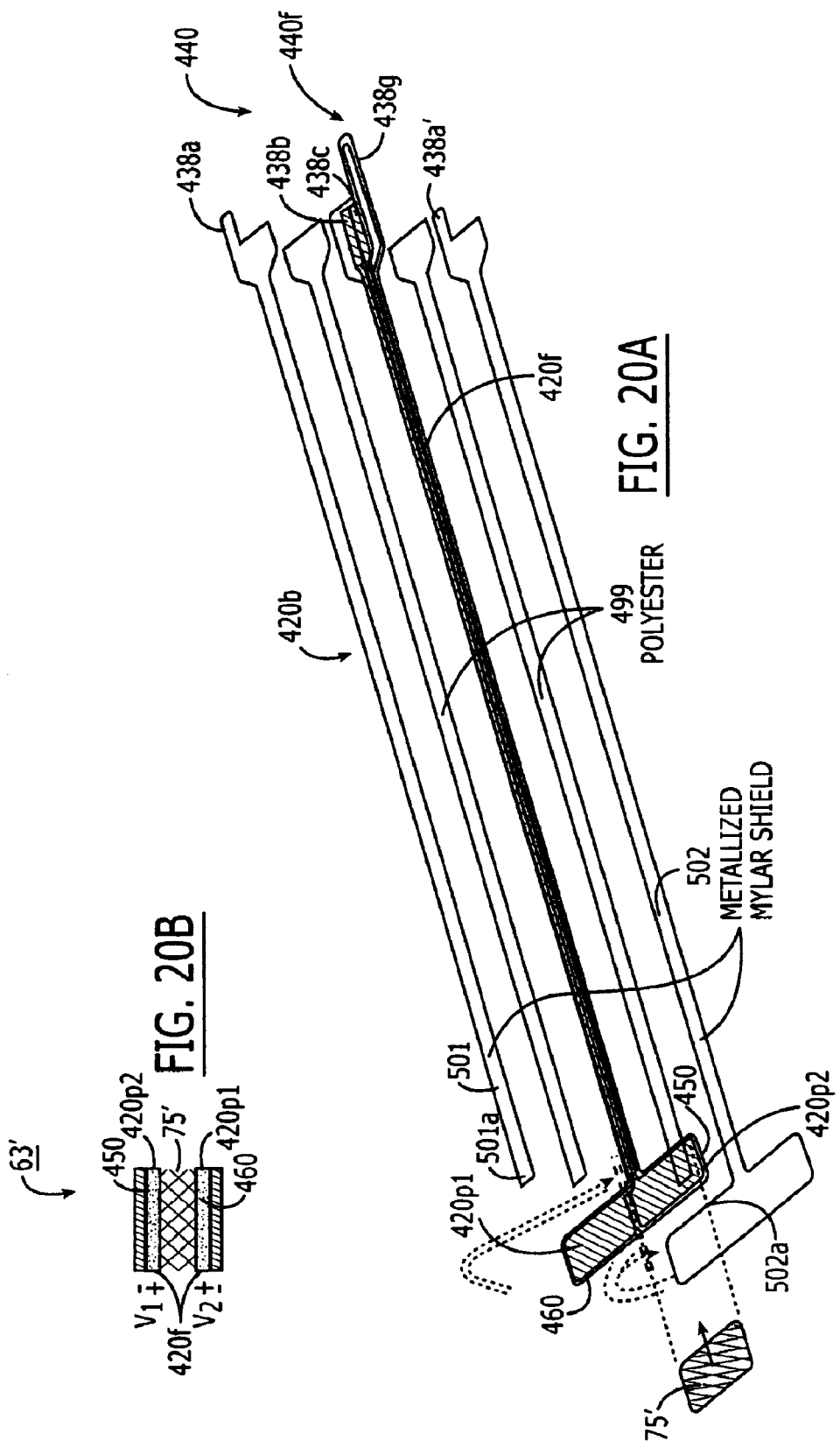

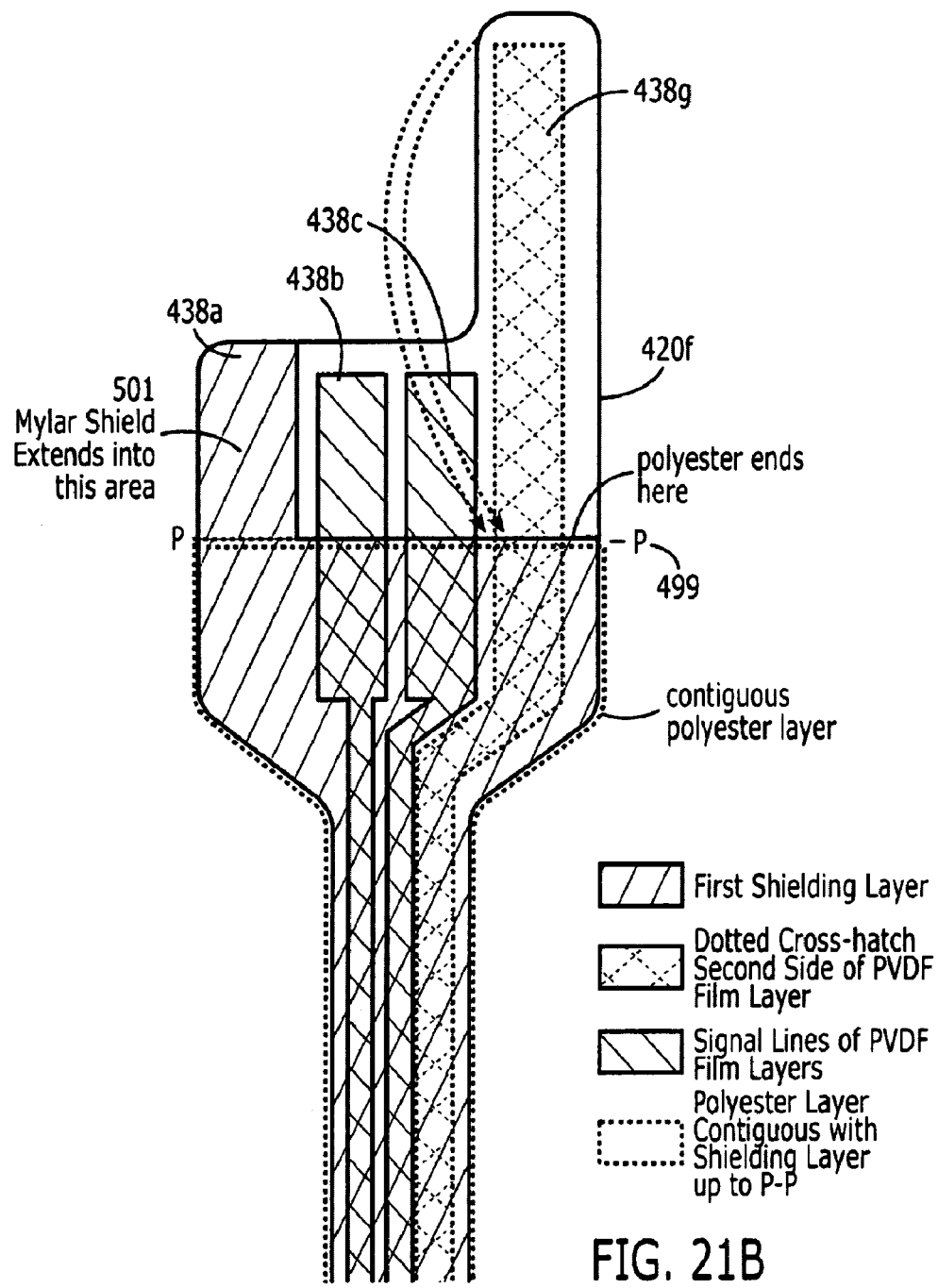

LOW PROFILE ACOUSTIC SENSOR ARRY AND SENSORS WITH PLEATED TRANSMISSION LINES AND RELATED METHODS

RELATED APPLICATIONS

This application claims priority from International PCT Application Serial No. PCT/US00/05124 filed 29 Feb. 2000, which claims priority from U.S. Provisional Application Ser. No. 60/122,264 filed 1 Mar. 1999 and U.S. Provisional Application Ser. No. 60/132,041 filed 30 Apr. 1999; the international application was published in English under PCT Article 21(2). The contents of these applications are hereby incorporated by reference as if recited in full herein.

FIELD OF THE INVENTION

The present invention relates generally to disposable acoustic sensors for capturing sounds from within the human body. The acoustic sensors are particularly useful for non-invasive digital acoustic cardiography, phonography, and acoustic spectral analysis applications.

BACKGROUND OF THE INVENTION

Recently, acoustic sensors have been used for the non-invasive detection of coronary artery disease. See co-assigned and co-pending U.S. patent application Ser. No. 09/188,510 entitled "Non-Invasive Turbulent Blood Flow Imaging System," the contents of which are hereby incorporated by reference as if recited in full herein. Generally stated, in operation, sensors are configured on a patient's chest (i.e., contacting the external epidermal surface or skin) to generate an electrical signal in response to a detected acoustic wave. The detected acoustic wave signals are processed to identify features that indicate the condition of a patient's coronary arteries, specifically the presence or absence of lesions that limit the flow of blood through the coronaries. An essentially uniform display indicates normal blood flow, while a non-uniform display may indicate abnormal (turbulent) blood flow and/or the presence of an occlusion.

In the above-described non-invasive systems, the acoustic sensors are positioned over the chest cavity in an acoustic window as described in co-pending and co-assigned U.S. patent application Ser. No. 09/188,434 entitled, "Acoustic Sensor Array For Non-Invasive Detection of Coronary Artery Heart Disease," the contents of which are hereby incorporated by reference as if recited in full herein. In position, the sensors are preferably configured over the intercostal space so as to reliably generate data signals corresponding to the blood flow of the patient during each phase of the cardiac cycle. The acoustic sensor is preferably designed to sense the flexing of a patient's external epidermal surface (skin) that is a result of the localized nature of the internal heart sounds. The sensor is also preferably easy to position on a patient and inexpensive such that it can be a single use device, which is disposable after use. In operation, the sensor is preferably configured to be conformal to the chest configuration of a patient (which varies patient to patient) and is also preferably configured to generate the electrical signal based on the flexure of the skin. Unfortunately, poor correlation of signals from improper sensor positioning, array geometry, and/or sensor configurations can adversely affect the reliability and/or correlation of the detected acoustic signal. Indeed, one potentially problematic sensor characteristic is that it can generate signals which are not representative of the interested acoustic wave associated with the blood flow of a patient, i.e., it can be responsive to extraneous acoustic waves and noise.

Conventional acoustic sensors can have poor signal to noise ratio (SNR) in that they can be unduly sensitive to environmental noise (typically requiring a special, quiet room be used for acoustic applications) or can suffer from low sensitivity relative to its electrical floor. Other sensors have other performance deficiencies such as inadequate sensitivity. In addition, many sensors are relatively complex configurations which can make them expensive to produce and difficult to apply clinically.

An example of a conventional disposable acoustic pad sensor is illustrated in U.S. patent application Ser. No. 08/802,593. The sensor includes a plurality of layers of various materials connected at one end to a substantially rigid electrostatic shield and electrical connector. Another example of an acoustic sensor is shown in U.S. patent application Ser. No. 09/136,933. This sensor is a flexible thin-film sensor which includes a foot portion and a two-piece piezoelectric film support. Still other examples of acoustic sensors are described in U.S. Pat. Nos. 5,365,937, and 5,807,268. These sensors employ an air gap and a frame which acts to stretch and hold a polymer film in tension. However, there remains a need to provide improved sensors for the efficient and improved passive detection of heart and blood-flow acoustics.

OBJECTS AND SUMMARY OF THE INVENTION

It is therefore an object of the present invention to provide an improved low profile sensor which is configured to be substantially conformal to a patient's external epidermal surface.

It is an additional object of the present invention to provide an improved sensor which provides a high signal to noise ratio for the acoustic energy of interest.

It is another object of the invention to provide an improved disposable sensor array with a plurality of individual sensor elements which are conformal to the underlying epidermal surface when positioned on a patient and which are proximately positioned one sensor to the next in a manner which allows an increased number of sensor elements within an acoustic region of interest and which positions the individual sensor elements such that they are separately responsive to preferred acoustic wave lengths.

It is an additional object of the invention to provide a sensor array which reduces the potential for undesired signal crossover along the separate electrical paths for the sensor elements.

It is yet another object of the invention to provide a transmission path for each of the individual sensors in a sensor array in a manner which reduces mechanical and electrical crossover between the sensors and/or external mechanical input into the sensor signal path.

It is another object of the invention to provide an improved method and device to install and align discrete sensor elements onto a subject.

These and other objects of the present invention are provided by a low profile acoustic sensory array which acts as a mechanical filter to minimize the sensor's signal activation or response to extraneous and/or undesired acoustic wavelengths or non-relevant acoustic wave components. Such a device is selectively responsive to short wavelengths that cause flexure through the thickness of the sensor, while resistant to longer acoustic wavelengths. The longer wavelengths are typically associated with compression waves in the body or in ambient noise within the examining room, and which can cause compression through the thickness of the sensor. In operation, due to the differences in the speed of the waves over a frequency band, shear waves typically have much shorter wavelengths than the wavelengths associated with compression waves. Stated differently, the sensor of the present invention is responsive to the flexural mode of displacement created by short wavelengths of shear waves, and substantially non-responsive to acoustic inputs of the much longer compression wavelengths.

Thus, one embodiment of the present invention provides a low profile flexural responsive sensor array which is sized and configured to substantially reject compression energy while responding to shear energy in the frequency range of interest. The sensor array includes a plurality of proximately positioned sensor elements. Preferably the sensor elements include two active surfaces, each of which lies on opposite sides of a neutral layer, such that the sum of the two layers produces a signal responsive to the flexure or change in curvature of the underlying surface since, in operation, they are displaced from the neutral axis of the structure.

More particularly, a first aspect of the invention is directed toward a low profile acoustic sensor array. The array includes a plurality of longitudinally extending sensor strips. Each of the sensor strips comprises a sensor frame having at least one longitudinally extending rail having a length. The sensor strips also include a plurality of acoustic sensor elements attached to the at least one rail. The sensor element has a pliable configuration. The strips also include a plurality of separate electrical signal paths, at least one (and in a preferred embodiment, two spatially separate and opposing paths) for each of the sensor elements. The electrical signal paths define a signal path from a respective one of each of the sensor elements to a desired end electrical termination point.

Preferably, the sensor array signal path is configured such that each sensor element includes first and second PVDF film layers and an intermediate neutral core, each PVDF film layer has an associated internal PVDF film surface (defining the live signal paths and electrodes), and corresponding first and second external ground surfaces (forming the ground plane).

In a preferred embodiment, the frame is configured with first and second transversely opposing sides. The opposing sides of the frame are spatially separated along a major portion of the frame length and each of the sensor elements is attached to a selected one of the frame sides. In this embodiment, the acoustic sensor element is sized and configured to extend between the sensor frame opposing sides. It is also preferred that the sensor elements are arranged on the frame such that adjacent elements are attached to different sides of the frame. Preferably, each of the strips is a unitary body along a major portion of its length, and the sensor elements are linearly aligned along the strip.

Another aspect of the present invention is directed toward an individual acoustic sensor element. The acoustic sensor element comprises a resilient core layer, preferably comprising a low permittivity material, having a core thickness and a first pliable material layer overlaying and contacting the core layer. The first pliable material layer comprises a piezoelectrically active material and has opposing internal and external surfaces. The sensor element also includes a second pliable material layer overlaying and contacting the core layer opposite the first pliable material layer. The second pliable layer comprises a piezoelectrically active material and also has opposing internal and external surfaces. The first material layer includes a first electrical trace disposed on the internal surface and the second material layer includes a second electrical trace disposed on its internal surface. During operation, and in response to flexure of said sensor element, the first and second electrical traces generate respective first and second voltages and the first and second voltages have opposing polarity.

In a preferred embodiment, the core comprises neoprene and the first and second pliable layers are formed from PVDF. Also preferably, the core layer has a first relative permittivity and the first and second pliable material layers have a second relative permittivity. The first relative permittivity is less than the second relative permittivity. As such, the resulting capacitance of the core may be such that it is about an order of magnitude less than the PVDF. In a preferred embodiment, the core is sized to have a greater thickness than the PVDF layers.

Capacitance is related to the permittivity ($\epsilon$), the area (A) and the thickness (1), as stated by the equation ($C=\epsilon A/1$); therefore, the core is preferably configured to have a capacitance which is less than that of the PVDF layers. As such, the sensor configuration will be such that the two permittivities typically differ by about a factor of two (because the core is configured to be thicker than the PVDF).

An additional aspect of the present invention is similar to the multiple strip array but is directed toward a single acoustic strip sensor array, the single strip array comprises a sensor frame having a frame length with at least one longitudinally extending rail. The strip also includes a plurality of sensor elements attached to the rail. The sensor element has a pliable configuration. The strip also includes opposing spatially separate first and second electrical signal paths for each of the sensor elements. The first and second electrical signal paths define a first and second signal transmission path from a respective one of each of the sensor elements to a desired end electrical termination point. Preferably, the acoustic strip sensor defines a substantially planar profile along at least the frame when viewed form the side. In a preferred embodiment, the frame and sensor elements are sized and configured (during operation and in position on a patient) to flex in response to flexural movement associated with shear waves while undergoing gross translation in response to long compressional waves (thus inhibiting sensor response associated with the long compressional waves). Preferably, the size of the acoustic strip sensor elements are such as to allow intercostal placement on the subject. In particular, each sensor element is sized and configured with dimensions of from about 8 mm to about 11 mm in length and width may be suitable, however, other sizes may also be utilized. It is also preferred that the first and second electrical signal paths are positioned to face each other on opposing sides of the core. In an alternative preferred embodiment, a discrete mass or stiffener is positioned to overlay each of the sensor elements.

Another aspect of the present invention is directed toward an acoustic coronary artery detection method employing the differential signal output associated with a flexed sensor as described above.

Yet another aspect of the present invention is directed toward a method for fabricating a strip sensor. The method includes the steps of forming a unitary body strip sensor foundation layer and forming a series of proximately positioned non-contacting pads and a frame segment into the foundation layer. Two separate opposing PVDF layers are positioned on opposing major surfaces of the foundation layer. The PVDF layers include two major surfaces and an electrical signal path formed on one surface and a ground path formed on the other. The method also includes the step of orienting the PVDF layers such that the electrical signal paths of each of the PVDF layers faces the foundation layer. Preferably, a series of corresponding but electrically separate external traces are disposed onto the major surfaces of the PVDF layers.

Preferably, the PVDF layers are selectively "actively" polarized about the sensor pad regions and substantially non-activated about the longitudinally extending sides or rails. Optionally, predetermined portions of the longitudinally extending sides can be heated to depolarize selective areas of the longitudinally extending sides or rails. In a preferred embodiment, a conductive outer ground plane is formed over the PVDF material such as by depositing a conductive material layer or forming metallized mylar over the top and bottom of the PVDF material surfaces (the surfaces facing away from the core).

An additional aspect of the present invention is directed to an accordion-pleated discrete or unitized element sensor array. More particularly, this aspect is directed to an acoustic sensor array which comprises a plurality of unitary acoustic sensor elements and a plurality of transmission lines having opposing first and second ends and defining a length therebetween, a respective one transmission line for each of the plurality of unitary acoustic sensors. The first end of the transmission line is individually attached to one of the acoustic sensor elements. Each of the transmission lines is configured with a series of undulations along its length. In a preferred embodiment, the undulations are a series of continuous pleated segments.

Another embodiment of the present invention is directed to an acoustic sensor. The acoustic sensor comprises a sensor element and a transmission line. The sensor element comprises a resilient core layer comprising a low permittivity material having a core thickness and a first pliable material layer sized and configured to sandwich and overlay the core layer. The first material layer comprises a piezoelectrically active material having opposing first and second major surfaces. First and second electrical traces are disposed on the first major surface of the first pliable material layer. The first pliable layer and associated electrical traces define a respective first and second electrode such that when in position over the core, the first electrode has an opposite polarity relative to the second electrode. Preferably, the sensor element also includes an exterior conductive shield layer sized and configured to overlay the second major surface of the first material layer.

The sensor additionally includes a linear transmission line attached to the sensor element. The linear transmission line includes first and second ends and longitudinally extends therebetween. The transmission line comprises a first pliable material layer extending from the first end to the second end of the linear transmission line. The first pliable layer has opposing first and second major surfaces and comprises a piezoelectrically active material. The transmission line also includes first, second, and third electrical traces disposed on the first pliable material layer in electrical communication with the sensor element first material layer electrical traces. The first and second electrical traces are disposed on the first major surface and the third electrical trace is disposed on the second major surface. The transmission line also includes first and second layers of a non-conducting film configured and sized to overlay a major portion of the first and second major surfaces of the first pliable material layer. The transmission line additionally includes a first linear outer layer conductive strip configured and sized to overlay a major portion of the first non-conducting film layer opposing the first major surface of the first pliable material layer and a second linear outer layer conductive strip configured and sized to overlay a major portion of the second non-conducting film layer opposing the second major surface of the first pliable material layer. The first pliable material layer of the transmission line and the sensor element is a unitary layer and the third electrical trace of the first pliable sensor having a sensor pad region and a transmission line, comprising the steps of configuring a first unitary layer of PVDF film having first and second opposing major surfaces with a laterally extending region having a first width and a longitudinally extending region having a second width. Electrical traces are formed onto the first major surfaces of the PVDF layer. The sensor electrical traces are arranged as rectangular shapes onto the lateral region of the PVDF layer such that the lateral region defines first and second separate electrode regions with opposing polarity. Electrical traces are formed onto the longitudinally extending region of the first and second major surfaces of the PVDF layer to define three electrical paths. The first and second paths are formed on one major surface to provide the electrical signal path for the first and second electrode regions, and the third path is formed on the opposing major surface of the PVDF layer and is configured with a primary finger portion. A resilient core is inserted onto a surface of one of the electrode regions and non-conducting film is positioned to overlay substantially the entire length of both major surfaces of the longitudinally extending region of the PVDF layer. A first electric shield material is positioned to overlay the non-conducting film on the side opposing the first major surface of the PVDF film. The first electrical shield includes a conductive secondary finger portion. A second electric shield layer is provided. The second shield layer is configured and sized to mirror the PVDF film shape and is positioned to overlay the second major surface of the PVDF film in the laterally extending electrode region and to overlay and contact the non-conducting film in the longitudinally extending region. The laterally extending region of the PVDF film is folded over the core such that the first and second electrode regions are positioned opposing the other with the core is positioned intermediate thereof. The primary finger of the ground strip is folded over to provide a terminal connection for the ground. The shield material thereby provides a substantially continuous electric shield for the externally exposed sensor body. Preferably, the method also comprises the step of forming undulations along a portion of the length of the longitudinally extending region.

Each of the sensors or sensor array embodiments of the present invention may also include one or more discrete masses or stiffeners positioned in one or more regions of the of sensor element to facilitate the flexural response of the sensor. Preferably, the discrete masses or stiffeners are positioned on the external surface (away from the patient's skin) and can include a reflective surface to allow photogrammetric alignment means for the convenient operation of the detection system. In one preferred embodiment, the discrete mass is about 5 grams of high-density material and is laterally positioned to extend in a central region across the width of the sensor pad. Advantageously, this discrete mass can improve the sensitivity of the sensor element over a frequency band of interest, particularly the frequency band used in the passive analysis of coronary-generated acoustic sounds.

The present invention is advantageous because the low profile sensor array allows for a low center of gravity, is relatively easy to manufacture, and is resiliently configured to be conformal to the epidermal outer layer. In addition, the low profile sensor can act as a mechanical filter such that it is responsive to shear waves but relatively non-responsive to compressive wavelengths in the frequency range of interest.

Further, the strip array sensor of the instant invention is configured in a smaller package with a substantially constant and flat profile and is advantageously configured to allow additional sensors to be spatially positioned with separate electrical signal paths in close proximity, thereby allowing increased number of sensor elements to be positioned on a patient in the region of interest.

Alternatively, the instant invention configures a series of aligned but discrete conformal flexural sensors with correspondingly separate transmission lines which are configured to respond to shear waves while being substantially non-responsive to acoustic inputs of compression waves in the frequency range of interest (typically 100–1000 Hz). In a preferred embodiment, the transmission lines are flexible and configured with a means to substantially mechanically isolate or dampen the transmission line from the other sensors and transmission lines in the array in order to minimize any cross talk between the electrical sensor paths or to inhibit translation of undesired mechanical forces in the system operational environment. Also advantageously, a detachable carrier member can be used to minimize the installation or site preparation time needed by an operator to position multiple sensors onto a patient.

BRIEF DESCRIPTION OF THE DRAWINGS

FIG. 1A is a schematic illustration of a sensor array assembly according to one embodiment of the present invention.

FIG. 4 is side view of the sensor shown in FIG. 1B.

FIG. 5 is an enlarged partial top view of an alternate embodiment of a sensor array according to the present invention.

FIG. 5A is an enlarged partial top view of yet another embodiment of a sensor array according to the present invention.

FIG. 6 is a top view of a carrier unit or foundation structure according to a preferred embodiment of the present invention. FIG. 6 also illustrates heat applied to predetermined areas of the foundation structure to depolarize regions of the PVDF film on the frame.

FIG. 7 is a top view of a silk screen or external signal trace pattern according to the present invention.

FIG. 14a illustrates the substantial non-response associated with a longer wavelength transmitted across the sensor situs while FIGS. 14b and 14c show the voltage response (opposing polarity) corresponding to flexure at shorter wavelengths of interest. As shown, the voltage polarity corresponding to an upward flexure is positive for the upper PVDF layer and negative for the lower PVDF layer and the polarities reverse for a downward flexure.

FIG. 20A is an exploded diagram of a sensor body according to the present invention.

FIG. 20B is a sectional view of a sensor element according to the present invention.

FIG. 21B is a partial top view of a sensor body having multiple layers according to the present invention.

FIG. 25B illustrates a combination of added discrete mass and stiffeners according to the present invention.

DETAILED DESCRIPTION OF THE INVENTION

Figure 1B:
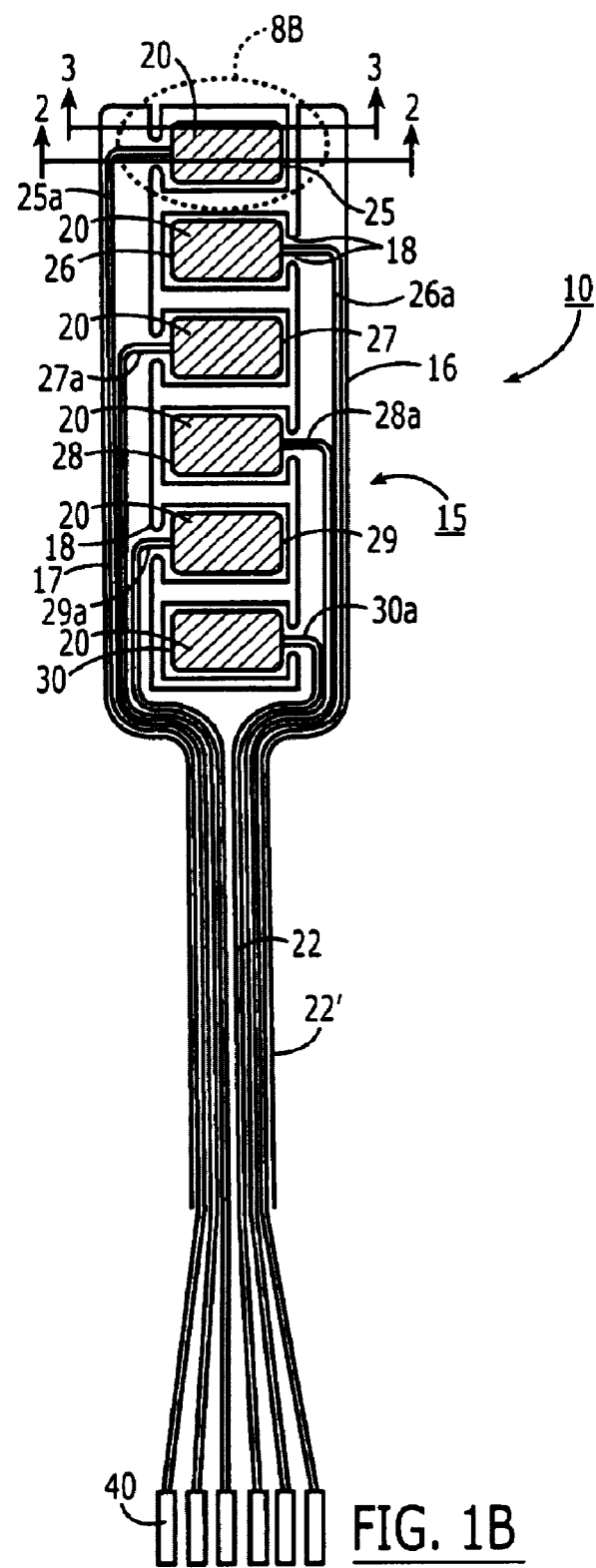
FIG. 1B is a top view of a low profile strip sensor array according to the present invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. In the drawings, layers or regions may be exaggerated for clarity.

The present invention relates to a sensor array configuration and components thereof and an associated method for fabricating a sensor array. In the description of the present invention that follows, certain terms are employed to refer to the positional relationship of certain structures relative to other structures. As used herein, the term "longitudinal" and derivatives thereof refer to the general direction defined by the longitudinal axis of the sensor array that extends between the two ends of the sensor array. Thus, when positioned on a patient, the longitudinal axis will extend along the length of the strip sensor. As used herein, the terms "outer", "outward", "lateral" and derivatives thereof refer to the general direction defined by a vector originating at the longitudinal axis of the sensor array and extending horizontally and perpendicularly thereto. Conversely, the terms "inner", "inward", and derivatives thereof refers to the general direction opposite that of the outward direction. Together, the "inward" and "outward" directions comprise the "transverse" direction.

Referring now to FIG. 1B, a preferred embodiment of a low profile sensor array 10 according to the present invention is illustrated. The sensor array 10 is configured to inhibit the sensor elements' 20 response to compression energy to provide a selective output which represents substantially only the acoustic energy of interest (shear waves having short wavelengths in the acoustic frequency band of interest). Preferably, the sensor elements 20 include two electrically active layers, each of which lies on opposite sides of a neutral layer, such that the voltage output of the two layers produces a signal output responsive to the flexure or change in the change in curvature of the underlying surface. As such, the sensor array 10 is configured to act as a mechanical filter to filter the sensor's response to compression energy.

Figure 9:
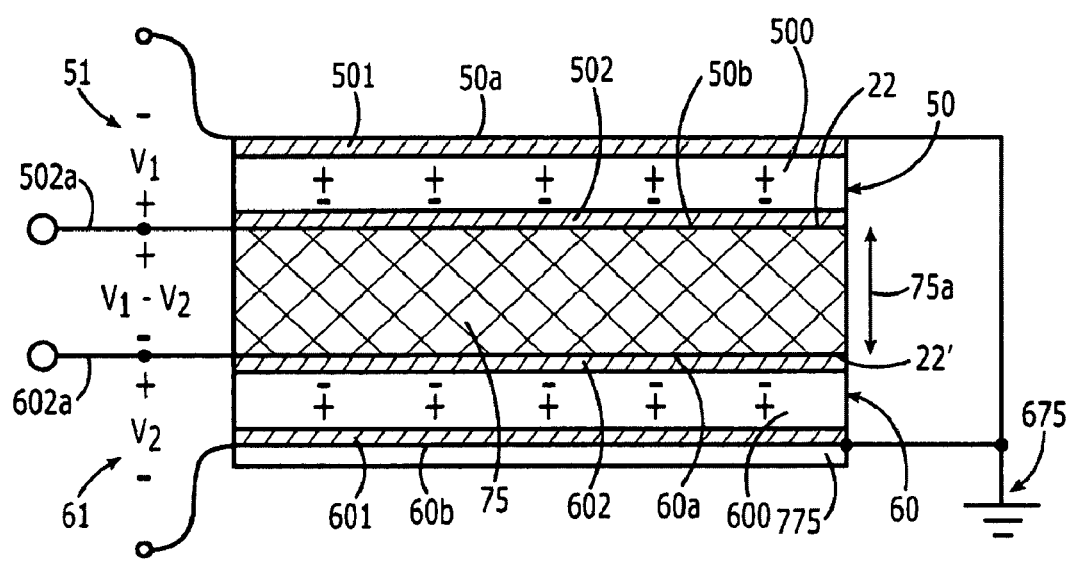
FIG. 9 is a schematic of a partial sectional view of the sensor element taken along lines 9—9 of FIG. 8B.

Generally described, the sensor array 10 includes a frame 15 and a plurality of sensor elements 20. The sensor array 10 is configured with a center core layer 75 and opposing (PVDF) outer layers 50, 60 which include piezoelectric layers 500 and 600. As shown in FIG. 9, each of the (PVDF) outer layers 50, 60 provides a pair of spatially separated electrodes 501, 502, and 601, 602 which define first and second signal voltages 51, 61 with respect to ground 675. As is also shown in FIG. 9, each of the outer layers 50, 60 have an external surface 50a, 60b which is electrically tied to the same electrical ground 675. The two opposing outer layer electrode surfaces 501, 502 and 601, 602 are configured to provide separate electrical signal paths (i.e., voltage outputs $V_1$, $V_2$, respectively) when the sensor 20 is flexed as will be discussed further below. The signal surfaces 50b, 60a are preferably provided by positioning signal traces 22 (FIG. 7) on the appropriate surface of the PVDF layer 50, 60. That is, as shown, the inner facing surfaces of the PVDF layers 50b, 60a, include electrical traces formed thereon.

The outer ground plane or surfaces 675 are preferably provided by applying a conductive layer onto the outer faces of the PVDF layers 50a, 60b. For depositing or forming the electrical traces 22, 22' or the ground surface, any metal depositing or layering technique can be employed such as electron beam evaporation, thermal evaporation, painting, spraying, dipping, or sputtering a conductive material or metallic paint and the like or material over the selected surfaces of the PVDF layers 50, 60. The ground plane is preferably formed by applying a continuous metallized surface over the entire outer surfaces of the PVDF layers 50a, 60b to form a continuous shield. Of course, alternative metallic surfaces or techniques can also be employed such as by attaching a conductive mylar shield layer over the outer surface of the PVDF layers 50, 60. Preferably, conductive paint or ink (such as silver or gold) is applied to the PVDF layers as a thin planar layer such that it does not extend above or around the perimeter edge portions of the signal paths of the internal traces 22, 22'.

As shown in FIG. 1B, the sensor array 10 includes a frame portion 15 with two longitudinally extending side rails, a first side rail 16, and a second side rail 17. Preferably, the frame 15 is configured such that the two side rails 16, 17 are spatially separate along a major portion of the length of the frame 15.

A plurality of sensor elements 20 are positioned intermediate the two side rails 16 and 17 such that each sensor element 20 is attached to at least one of the sides 16, 17. Preferably, as shown, each sensor element 20 is attached to only one side, ie., at a lateral attachment 18 positioned either at the first side 16 or the second side 17. Further preferably, as shown in FIGS. 1A and 1B, adjacent sensors are attached to different sides of the frame 15 and the lateral attachments 18 extend substantially about the center of the sensor element 20. As shown in FIGS. 1A, 1B, 2, 3 and 7, the sensor array 10 includes a first and second signal trace pattern 22, 22'. The trace patterns 22, 22' are the same and are configured to define two separate but corresponding active sensor electrical signal regions 25, 26, 27, 28, 29, 30 and 25', 26', 27', 28', 29', 30' across the upper and lower PVDF film layer sensor elements 20, 20'. The sensor array 10 is configured such that each corresponding sensor element electrical signal region 25, 25', 26, 26', 27, 27', 28, 28', 29, 29' and 30, 30' has a separate and corresponding electrical signal path 25a, 25a', 26a, 26a', 27a, 27a', 28a, 28a', 29a, 29a', 30a, 30a' respectively, defining corresponding but separate upper and lower signal paths 51, 61. As such, the electrical path for each sensor 25a–30a extends from a sensor element 20 to an electrical termination or electrical connection pad 40. Although FIG. 1A illustrates only one PVDF signal layer, the opposing PVDF layer of the sensor array 10 includes another (second or bottom) signal trace pattern 22' substantially similar to and configured to align with the top external trace 22 pattern shown, including corresponding primed element numbers. That is, upon assembly or fabrication, two of the PVDF layers shown in the left side of FIG. 1A are disposed on opposing sides of a neutral core 75.

In a preferred embodiment, the electrical traces 22, 22' are applied to the respective PVDF outer layer 50, 60 such as by applying a silk screened conductive ink or paint pattern. The ground plane is preferably provided on each PVDF layer 50, 60 by applying a continuous layer of conductive ink or paint thereon. The core 75 typically includes a neoprene layer with a thin film of adhesive on each side. The PVDF layers 50, 60 are then secured to the core 75 to sandwich the core therebetween. The electrical connections (pin terminations) are made in an external connector and the upper and lower PVDF ground traces or surfaces 50a, 60b are connected to a common ground 675 thereat. See U.S. Pat. No. 5,595,188, the contents of which is hereby incorporated by reference as if recited in full herein.

As shown in FIG. 5, the sensor array 10' includes a frame 15' which can be configured to provide supplemental structural attachments 21 at selected areas (such as at the ends) to further structurally tie the two sides 16', 17' together to help provide structural strength or positional integrity for the sensor elements on the array 10'. This can be beneficial for sensor arrays 10' which, once sterilized, are enclosed in a sterile underlying adhesive layer and sterile package for shipment and storage, as the sensor array is typically quickly peeled from its packaging during use. The additional mechanical reinforcement can minimize sensor element 20 displacement from the frame 15'.

FIG. 5A illustrates another preferred embodiment of a sensor array 10'' according to the present invention. As shown, the frame 15'' includes a single longitudinally extending side or rail 17'' which is preferably widened relative to the dual rail configuration shown in FIG. 1B to provide adequate physical separation (to minimize the potential for electrical coupling) of the electrical traces 22b. Of course, the electrical traces 22b will be altered to extend along the single rail 17''.

Figure 2:
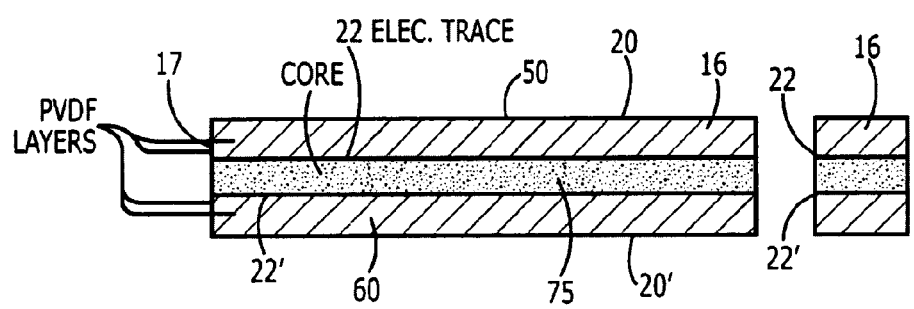
FIG. 2 is a cross-sectional view of the low profile sensor array taken along lines 2—2 of FIG. 1B.
Figure 3:
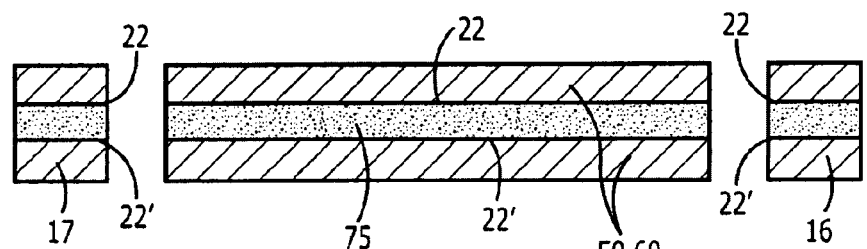
FIG. 3 is a cross-sectional view of the low profile sensor taken along lines 3—3 array of FIG. 1B.

FIGS. 2 and 3 illustrate a section view of a preferred embodiment of the low profile sensor array 10. As shown (in sectional view), the sensor array 10 is configured such that the two piezoelectrically active (PVDF) outer layers 50, 60 of the sensor array 10 (including the outer layers of both the frame sides 16, 17 and sensor elements 20) comprise a first material having an associated first thickness while a core or intermediate layer 75 comprises a second resilient material having a second thickness. FIG. 9 schematically illustrates the electrical configuration of the sensor element 20 and will be discussed further below. The external traces 22, 22' are positioned on the respective top and bottom surfaces 50b, 60a (i.e., the interior surfaces on a completed array assembly) of the outer layers 50, 60.

As shown, the core 75 thickness is greater than the thickness of the outer layers 50, 60. In a preferred embodiment, the core 75 is an order of magnitude thicker than the outer layer thickness. More preferably, the core 75 has a depth or thickness of about 600 microns while the outer layers 50, 60 are about 30 microns thick. It is also preferred that the core material be selected such that it has a relative permittivity which is less (and more preferably much less such as an order of magnitude less) than the relative permittivity of the outer layers 50, 60. In one embodiment, a suitable core relative permittivity value is about 5 or 6.

It is also preferred that the core material 75 be selected such that it is resilient or compliant (substantially incompressible material) and preferably has low viscous losses. "Resilient", as used herein, means that the core is sized and formed of a material which allows the sensor array (at least the sensor element) to be conformal to the underlying surface when in position. Stated differently, the core 75 is configured such that at least the sensor elements 20 are substantially compliance matched with the body, i.e., to follow the shape of the underlying patient skin surface when positioned thereon. Preferred core materials include nitrile, neoprene, latex, polyethylene, or high-density polyethylene forms. In a preferred embodiment, the core material is neoprene. Alternatively, the core 75 can be formed as a thin layer of insulator (a neutral center), allowing the two opposing electrically active layers 50, 60 to be electrically separated and directly responsive to the flexure of the underlying surface.

Figure 14A:
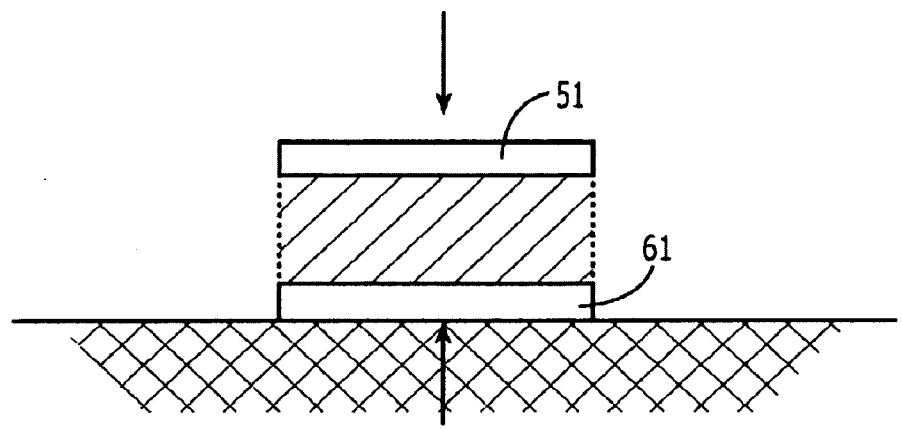
FIGS. 14a–14c illustrate a preferred embodiment of a sensor's electrical response.
Figure 14B:
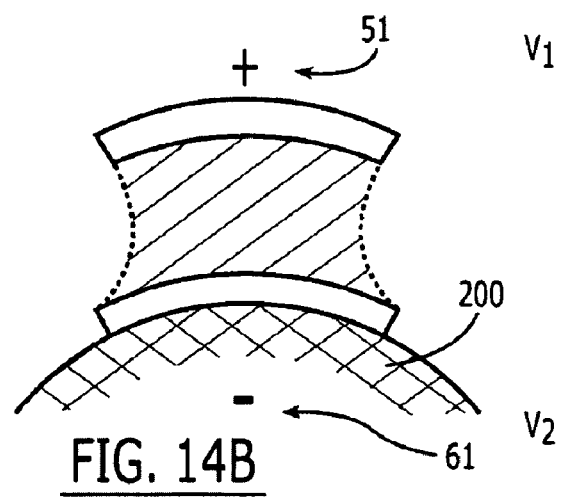
Figure 14C:
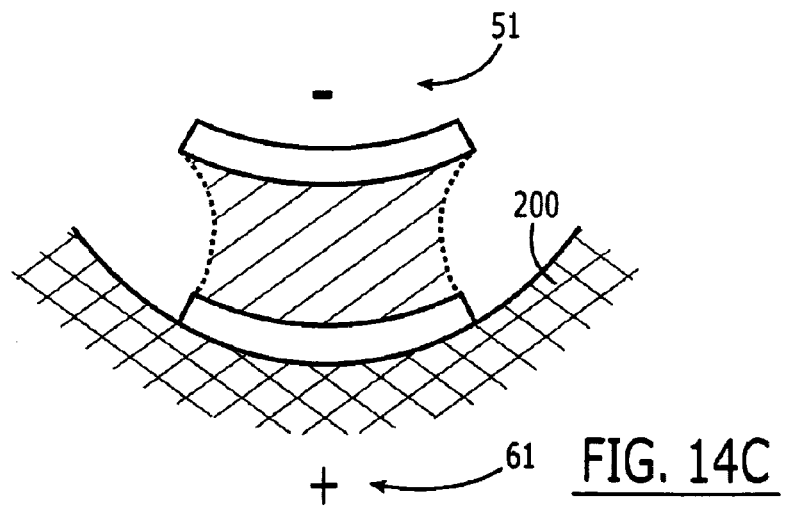

In a preferred embodiment, the core 75 has a first relative permittivity and the outer layers 50, 60 are first and second pliable material layers which have a second relative permittivity. The first relative permittivity is less than the second relative permittivity. As such, the resulting capacitance of the core 75 may be such that it is about an order of magnitude less than the PVDF layers 50, 60. In a preferred embodiment, the core 75 is sized to have a greater thickness than the PVDF layers 50, 60. The core 75 capacitance is related to the material and configuration of the core 75. More particularly, the core 75 capacitance is related to the core material permittivity ($\epsilon$), and the core configuration (area (A), and the thickness (1)) as stated by the equation ($C=\epsilon A/1$). In a preferred embodiment, the sensor 20 is configured such that the capacitance of the core 75 is less than that of the electrodes defined by the PVDF layers 50, 60. Referring to FIGS. 2, 3 and 9, the outer layers 50, 60 are formed from a piezoelectrically active material such as, but not limited to, polyvinylidene fluoride (PVDF) or its copolymer with trifluoroethylene (PVDF-TrFe). As shown in FIG. 9, electrodes 501, 502, 601, 602 are formed on both sides of the major surfaces of piezoelectric film 500, 600. In this way, the PVDF material provide outer layers 50, 60 which function as electrodes which can act as an electromechanical transducer and, as such, can be used as an acoustic sensor 20. Generally described, and as shown in FIGS. 14A, 14B, and 14C, the sensor 20 is configured such that when the piezoelectric material is subjected to strain or stress (flexure or curvature displacement) an electric potential or voltage proportional to the magnitude of the strain or compression is developed across the thickness of the piezoelectric material. See e.g., U.S. patent application Ser. No. 08/802,593, the contents of which is hereby incorporated as if recited in full herein. A preferred electrical configuration will be discussed further below.

Figure 26:
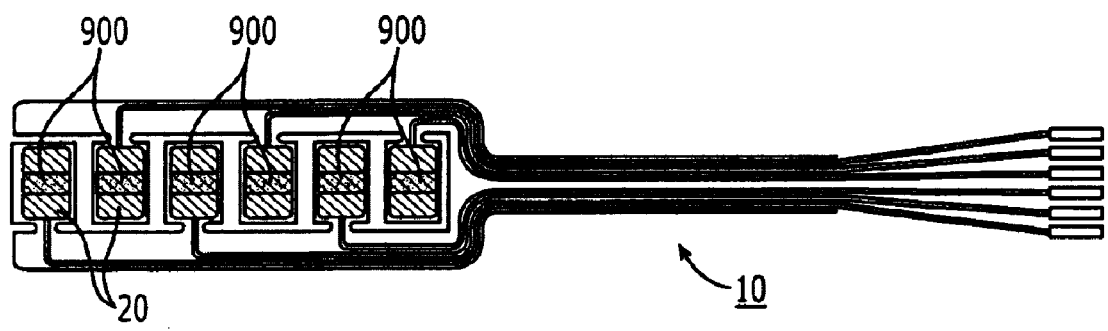
FIG. 26 illustrates a strip array with discrete masses according to the present invention.

FIG. 4 is a side view of a low profile sensor array 10 according to a preferred embodiment of the present invention. As shown, the sensor array 10 is configured such that each of the sensor elements 25–30 and the frame 15 are in (substantially) coplanar alignment along at least the top surface 10a of a major portion of the frame 15 region when viewed from the side (i.e., the sensors 20 and sides 16, 17 have the same material thickness and layers). More preferably, as shown, the sensor array 10 (and the sensor array 10'' with the single rail frame 15'') is configured such that the elements 20 and the frame 15 have the same profile configuration along the top and bottom surfaces 10a, 10b. The sensor array 10 is substantially flush across the top and bottom surfaces 10a, 10b. As shown, the linear strip array preferably includes a top and bottom outer surface 10a, 10b with a substantially constant and flat profile. Alternatively, as will be discussed further below, the top outer surface can include one or more discrete masses 900 or stiffeners 910 attached to the sensor element region to modify the response of the flexural sensor element 20 (FIG. 26).

FIG. 5 shows an alternate embodiment of a sensor array 10'. In this embodiment, the lateral attachments 18' extend about alternating forward and rearward edges of the sensor elements 20. Also as shown, the sides or side rails 16', 17' have a greater lateral length, providing additional area for the signal traces 22. The additional area can allow the separate paths to be spatially separated by a greater separation distance or can allow additional sensor elements 20 to be used (more area used for additional traces needed for the additional elements). The additional width of the sides 16', 17' can also help minimize electrical cross talk along the length of the signal path. Similarly, FIG. 5A illustrates a single-rail embodiment of a sensor array 10" according to the present invention. As shown, the sensor arrays 10, 10', 10" include a plurality of sensor elements 20 (preferably more than four sensor elements, and more preferably six or more sensor elements).

Turning now to FIG. 6, a preferred structural foundation layer 100 is shown. The foundation layer 100 provides the structural foundation for the signal traces 22, 22' which are preferably applied to the PVDF layers 50, 60 and attached to the foundation layer 100, as will be discussed further below. As shown, the foundation layer 100 defines the frame 15, the side rails 16, 17 and the pads for the sensor elements 20. It also includes a neck portion 102 which separates the frame upper portion which includes a resilient core material to a thinner ribbon portion 105 (which extends down to the terminal connection ends at the connector (not shown)). In any event, the neck portion 102 of the frame 15 is preferably configured to transition the sensor array from one thickness to another such that the core 75 has a first thickness at the neck upper portion 102 but substantially terminates prior to the end of the neck lower portion 105 to a second reduced thickness. Preferably, a shown in FIG. 6, the sensor array 10 is configured such that the neoprene extends down until the area shown in cross hatch. A preferred neoprene stop zone 76 is shown at position A—A. Preferably, the ribbon 105 is configured such that the PVDF electrically active surfaces do not contact. For example, other thin insulating core materials such as a double sided polyethylene film can be positioned such that it extends between the two inwardly facing surfaces of the PVDF layers 50, 60.

FIG. 7 illustrates a preferred trace pattern 22, 22' which is, upon assembly, positioned onto the appropriate surfaces of the film layers 50, 60 forming the respective electrical regions for the sensor elements 25–30, 25'–30' and respective signal paths 25a–30a, 25a'–30a' which extend down the neck portion 102 and ribbon portion 105 of the sensor frame. As shown in FIG. 7, the electrical pattern 22, 22' includes a sensor pad active region 220 and linear traces 221. The trace pattern is disposed onto the piezoelectric layers 50, 60 as described above. Preferably, it is formed by applying conductive ink, such as disposing onto the outer surfaces of the outer layers 50, 60 a silver ink silk screen pattern. While particular conductive patterns are illustrated in FIGS. 7 and 5A, alternative conductive patterns may also be used. For example, conducting paint, flex circuits, foil or other coating or metal deposition methods and techniques may also be employed. It is preferred that, if flex circuits are used, that they are configured or attached to the foundation layer 100 so as to be transparent to the structure of the sensor array to minimize any potential interference with conformance of the sensor element to the body.

For clarity, it will be understood that, according to the present invention, protective films or coatings may also be positioned over the PVDF "outer" layers forming the ground and signal planes (or traces) as long as they are applied so as to be substantially transparent to the operation of the sensor elements. Therefore, as used herein, the trace(s) 22, 22' or outer layers 50, 60 can include traces or layers which are covered with moisture barrier coatings, adhesives, or other materials and are thus not truly "external" or "outer" as described for ease of discussion herein.

Figure 8A:
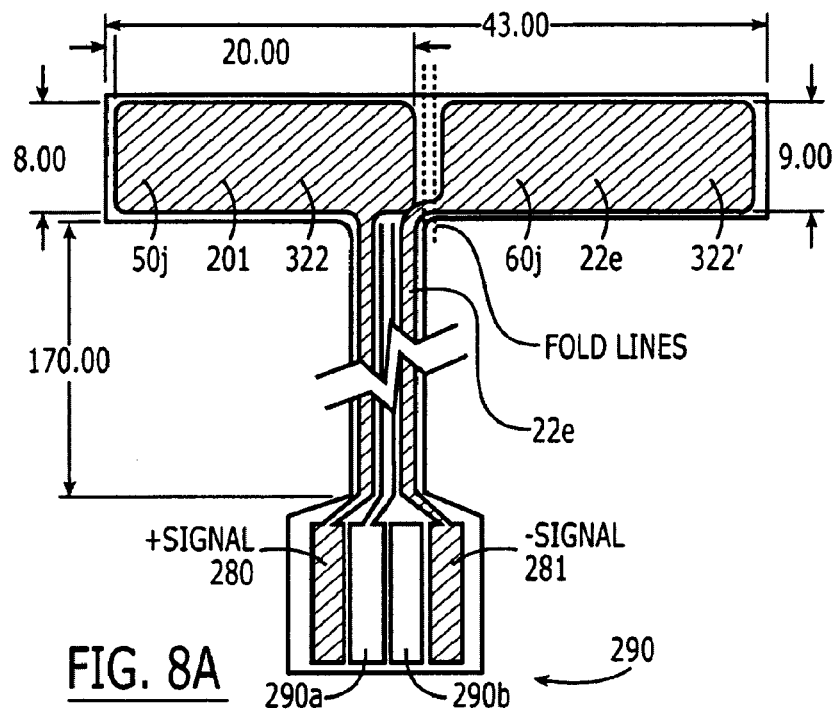
FIG. 8A is an enlarged top view of a single element sensor illustrating two electrode surfaces according to an alternate embodiment of the present invention. In this figure, the signal return covering the back of the PVDF film has been removed for clarity.
Figure 8B:
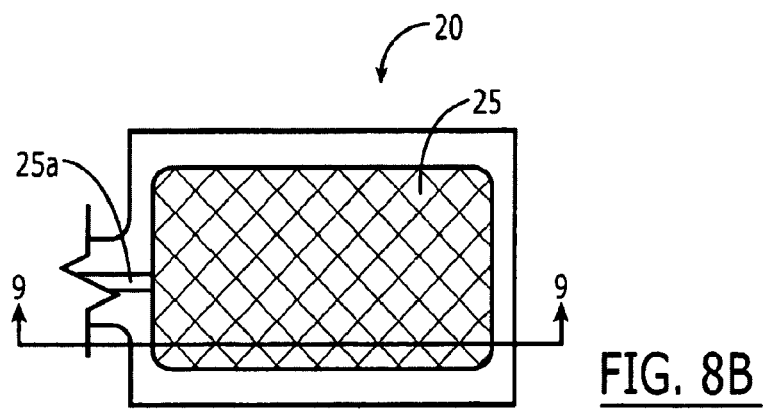
FIG. 8B is an enlarged top view of a sensor element shown in FIG. 1B.

FIG. 8B is an enlarged view of a sensor element 20. Preferably, the sensor element 20 is substantially rectangular with side dimensions of from about 8 mm to about 11 mm. In a preferred embodiment, as shown in FIG. 9, the upper and lower traces 22, 22' are deposited onto the inwardly facing major surfaces of the (PVDF) layers 50, 60. As such, the electrically active regions defining the signal paths include the pad regions 25, 25' and the signal lead paths 25a, 25a' which are spatially separated a distance from top to bottom about a central neutral core 75. The PVDF outer layers 50, 60 are preferably relatively thin (such as below about 60 microns, and preferably about 30 microns) while the core depth 75a is an order of magnitude greater (above 300 microns, and more preferably above about 500 or 600 microns). This configuration makes the thickness of the PVDF layer 50, 60 relatively structurally negligible compared to the depth or thickness of the core 75. As shown in FIG. 9, the upper and lower signal paths 502a, 602a defined by the trace patterns 22, 22' are separated by a distance which is substantially equal to the core depth 75a.

Figure 10:
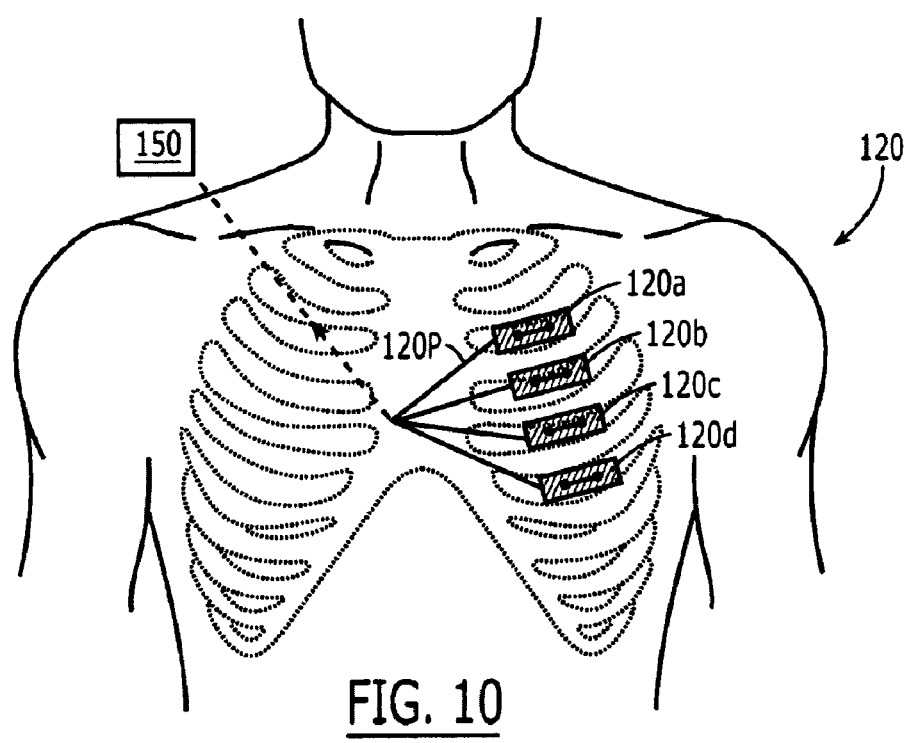
FIG. 10 illustrates a preferred array configuration positioned on the external skin or epidermal outer layer of a patient according to a preferred embodiment of the present invention.

FIG. 10 schematically illustrates a preferred configuration of a low profile sensor array assembly 120. As shown in FIG. 10, the sensor array assembly 120 includes four laterally positioned linear sensor or strip arrays 120a, 120b, 120c, 120d in electrical communication with a signal processor 150 (having an opto-isolator 151). FIG. 10 illustrates four sensor arrays 10 positioned over preferred intercostal spaces. See pending PCT and U.S. patent application Serial Numbers identified as PCT/US99/26198, 09/188,434 and 09/433,211, the contents of which are hereby incorporated by reference as if recited in full herein. FIG. 10 also illustrates a preferred pigtail arrangement for the sensor array assembly 120. As shown, the pigtail 120P preferably extends off the sensor elements toward the sternum of the patient, thereby allowing standard cord sizing notwithstanding the access to the patient (i.e., whether the system must be hooked to the patient from the right or left hand side of the bed). Alternatively, as shown in FIG. 11, the electrical pigtails 120P can extend from the opposing side.

Figure 11:
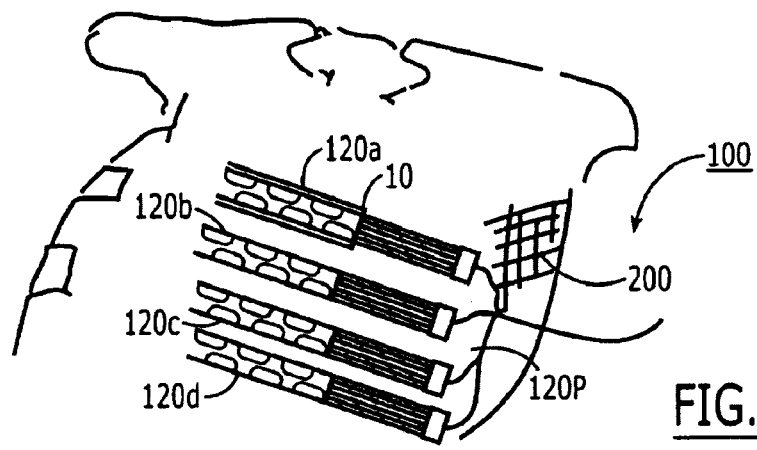
FIG. 11 illustrates a preferred array configuration with multiple strip array packages positioned in an acoustic window on a patient.
Figure 12:
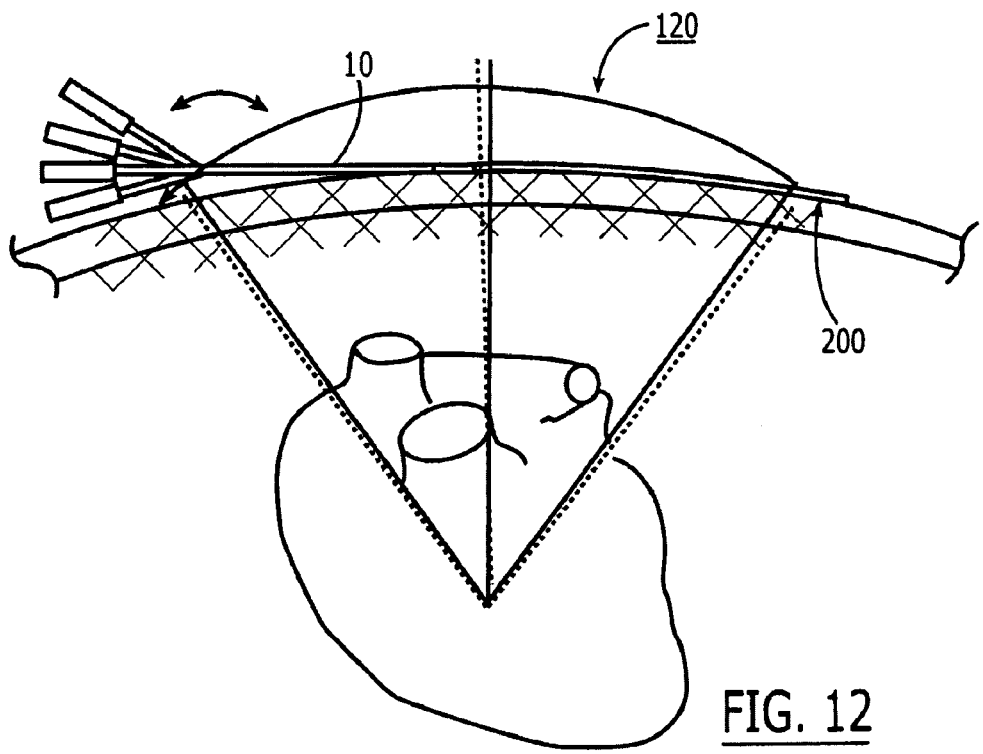
FIG. 12 is a side schematic view of the sensor array shown in FIG. 11.

Similarly, FIGS. 11 and 12 illustrate a preferred low profile sensor array 120 assembly positioned on a subject which comprises four linear array sensors 10, the sensors having six sensor elements 20 each. Of course, alternative numbers of sensor arrays 10 or sensor elements 20 on the arrays 10 can also be used (either in combination or alone). FIG. 12 illustrates the low profile acoustic sensor array 10 positioned on the skin 200 of a patient over an acoustic window above the cardiac region of interest. Thus, the sensor array according to the present invention preferably includes means for releasably securing the sensor array to a patient. Such means may comprise an adhesive layer which may be incorporated in or applied to one side of the sensor array such as the adhesive layer 775 shown in FIG. 9. Suitable adhesives for releasably securing medical apparatus or devices to a patient are known to those of skill in the art. As shown in FIG. 9, the sensor array 10 also preferably includes a release adhesive 775 positioned along a major portion of the lower external surface 60b to secure the sensor array to a patient during clinical use. Of course, sterile adhesive creams, double-sided tapes, and the like can alternatively or additionally be used to position the array on the patient's skin.

Turning now to FIGS. 9, 13A, 13B, and 14A–C, preferred electrical and operational schematics for the sensor elements 20 are shown. As discussed above, FIG. 9 illustrates the piezoelectric active outer layers 50, 60 as including a PVDF (or other piezoelectric polymer) portion 500, 600 and two corresponding opposing first and second interior active electrode surfaces or layers 501, 502 and 601, 602. The interior film surfaces 502, 602 each include a separate electrical signal path 502a, 602a while the outer film surfaces 501, 601 are tied to a common ground 675.

Figure 13A:
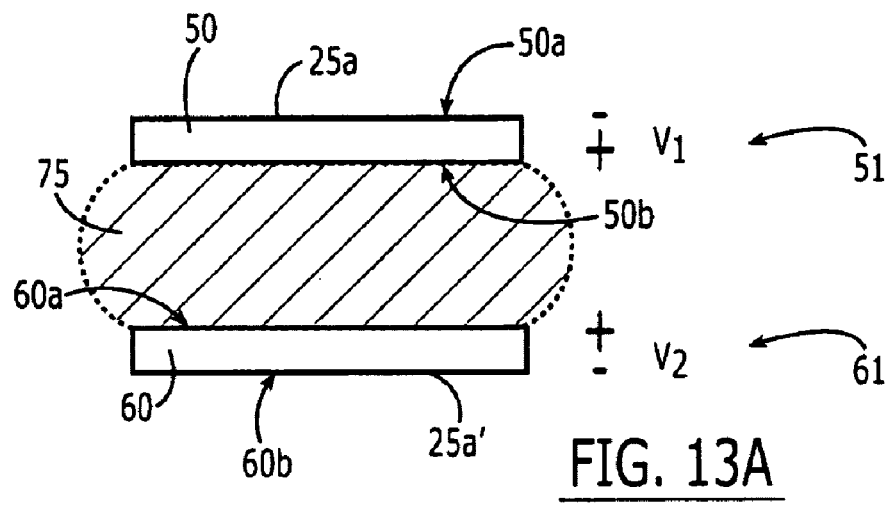
FIG. 13A is an electrical schematic of a sensor element according to a preferred embodiment of the present invention.
Figure 13B:
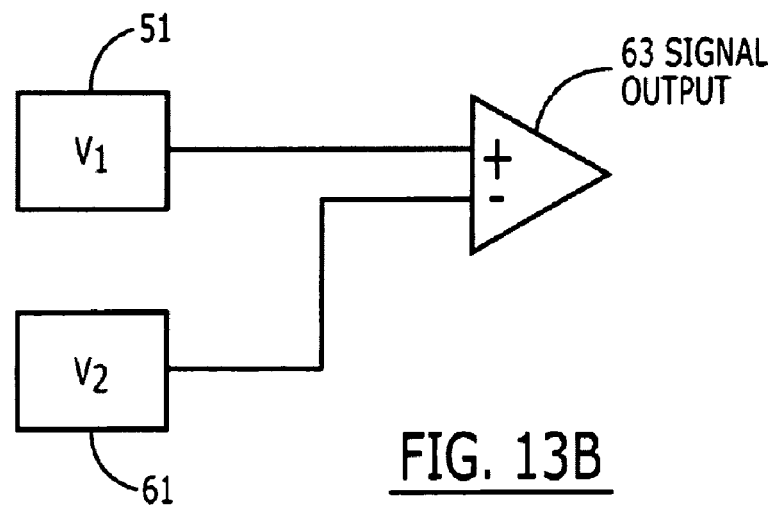
FIG. 13B schematically illustrates the sensor's voltage differential signal response corresponding to strain on the sensor configured as shown in FIG. 13A.

FIGS. 9 and 13A–B illustrate that the PVDF is disposed on the first (upper) outer layer 50 with a polarity of negative to positive. That is, the major inner surface 50b has a positive polarity while the major outer surface 50a has a negative polarity. In contrast, the PVDF is disposed on the (lower) outer layer 60 with the reverse polarity; positive on the major inner surface 60a, and negative on the major outer surface 60b. Of course, the layer polarities could also be reversed (i.e., the upper layer 50 can have negative to positive while the bottom layer 60 can have positive to negative).

As shown in FIGS. 14B and 14C, each of the outer layers 50, 60 provides a voltage ($V_1$ and $V_2$) 51, 61 in response to flexure of the sensor 20, respectively, even in response to long compressional waves. However, in response to gross translation of the sensor 20 which does not result in flexure, no voltage will result. Because the polarities are reversed, and because the core material and sensor configuration provides a high degree of coupling between the two outer 50, 60 active (electrical) layers, the absolute value of the voltages for a particular flex or curvature will be substantially the same. However, because during flexure or curvature of the sensor, one layer is in compression and the other layer in tension, the sign of the voltage will be opposite between the two layers. Further, if movement of the sensor does not result in curvature of the sensor, then the polarity of the sign will be the same between the two layers. Thus, the instant sensor configuration is preferably configured to read the voltage differential of the two voltages, that is the difference between the response voltages $V_1$, $V_2$.

Advantageously, as shown in FIG. 13a, the electrode configuration is such that the sensor 20 acts like a differential amplifier 63. In operation, the sensor array 10 takes the voltage differential of the two response voltages $V_1$, $V_2$ to generate a signal response which has an increased voltage value (approximately doubled value) and, thus, can provide improved SNR performance. Further, for non-flexure sensor excitation, the voltage polarities are such that the signal responses from each layer 50, 60 cancel each other, minimizing signal output for non-flexure excitations.

Thus, in operation, as schematically shown in FIG. 14a, for a non-strain input such as a compression wave (typically input to the sensors by ambient noise that is carried by noise in the air, or noise that is transmitted through structural vibration), both the top and bottom sensor layers see the same force, and without a strain or flexure to cause a curvature in the layers 50, 60 the polarity of the voltages are such that any signal response is cancelled and no signal output is transmitted for detection. In contrast, as shown in FIGS. 14b and 14c, the polarities of the layers 50, 60 associated with the strain in the PVDF or outer (electrical response) layers 50, 60 have opposing polarities. For example, for a given flexure in the outer layer 50, and a ($V_1$) response of 2 microvolts, the ($V_2$) response may be about (−2 microvolts), and the signal response for this flexure will then be 2−(−2) or 4 microvolts. Of course, the magnitude of the voltage will vary according to the degree of strain or curvature of the flexure.

FIG. 14a illustrates the substantial non-response associated with a compression or longer wavelength transmitted across the sensor situs while FIGS. 14b and 14c show the voltage response (opposing polarity) corresponding to flexure at shorter wavelengths of interest. As shown, the voltage polarity corresponding to an upward flexure is positive for the upper PVDF layer 50 and negative for the lower PVDF layer 60 and the polarities reverse for a downward flexure.

Figure 14D:
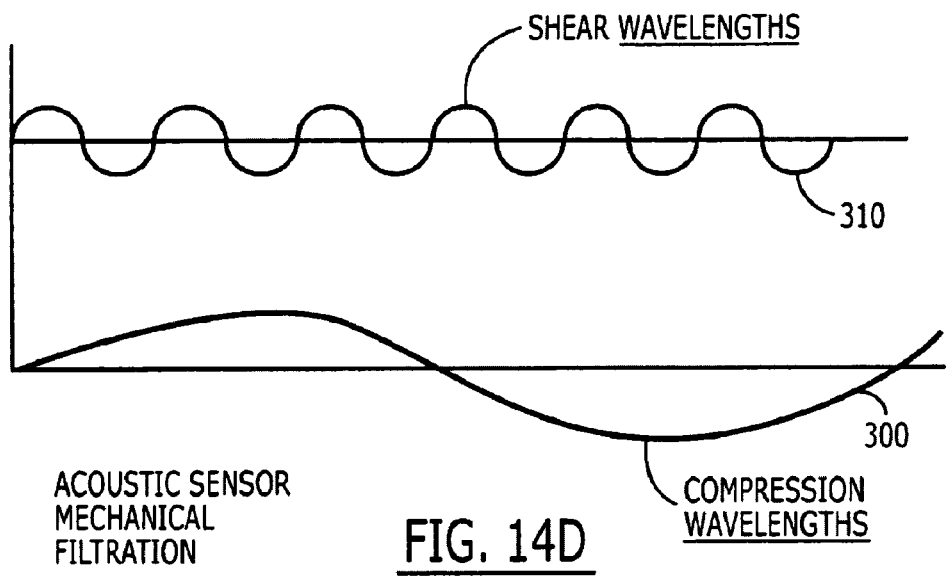
FIG. 14d schematically illustrates the sensor's ability to act as a mechanical filter to inhibit generating a detectable signal response for long wavelengths according to the present invention.
Figure 15:
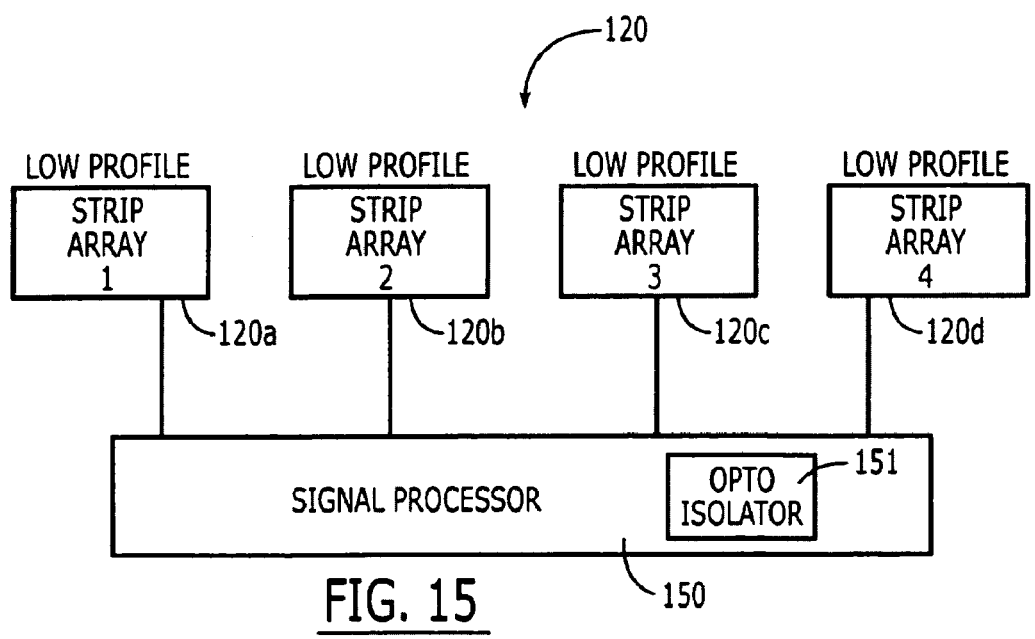
FIG. 15 illustrates a preferred sensor array system according to the present invention.

In a preferred embodiment, as schematically shown in FIG. 14d, the sensor arrays 10, 10', 10'', 10''' are configured such that they are selectively responsive to shorter wavelengths 310 that cause flexure through the thickness of the sensor element 20, 420, while being substantially non-responsive or resistant to longer acoustic wavelengths 300. The longer wavelengths 300 are typically associated with compression waves in the body or in the ambient noise within the examining room, and which cause compression through the thickness of the sensor element. In operation, due to differences in the speed of the waves or a frequency band of interest, shear waves typically have much shorter wavelengths than the wavelengths associated with compression waves. Stated differently, the sensor is responsive to the flexural mode of displacement caused by short wavelengths of shear waves 310, and substantially non-responsive to acoustic inputs of the much longer compression wavelengths 300. At the same time, the sensor array is configured to respond to shear waves having shorter wavelengths 310. Thus, the sensor array 10 of the present invention acts as a mechanical filter and inhibits or minimizes the sensor elements from generating a detectable signal response for long wavelengths at frequencies of interest. The sensors and sensor arrays described herein include an operational range for the acoustic wavelengths of interest for the diagnosis and detection of coronary artery disease. Preferably, the sensors include an operational range of at least about 100–2500 Hz, and more preferably a range of about 100–1000 Hz. Preferably, the sensor elements 20 are configured and sized on the frame 17 to respond to shear waves at the operating frequencies of interest such as those characterized as having propagation velocities of less than about 25 m/s, or more in the range of about 5–15 m/s, and to suppress or inhibit signal response for compressional waves or acoustic waves having a propagation velocity above about 100 m/s. More preferably, the sensor is configured to suppress response associated with the wave speed of compressional waves in the air, typically a velocity of about 340 m/s and the response associated with the wave speed of compressional waves in the body, the compressional wave velocities being typically about 1540 m/s in the body.

FIG. 8A illustrates an alternative discrete or single sensor embodiment of the present invention. The signal return covering the back of the film has been removed for clarity. It is preferred that the width of the pigtail be configured and sized to hold the capacitance of a signal trace below about 10% of that of a sensor element. As shown, the single sensor 201 includes a positive signal 280 and negative signal 281 electrical path which is formed by the two PVDF layers 50j, 60j similar to the electrical traces 322, 322' formed onto the outer PVDF layers of the strip array 10 discussed above. As shown, the single element 201 can be formed by configuring four signal lines on a single sheet of PVDF material. The single sheet is configured to be folded, such as along the dotted fold lines shown, to provide the two interior signal paths 280, 281 and the external common ground. The two grounds 290a, 290b are preferably formed by a metallized mylar shield 290 configured to provide a continuous planar electrical shield on one surface of the PVDF material (the surface opposing the electrical traces 322, 322'). The electrical pin out can also be alternatively configured as will be appreciated by one of skill in the art.

Figure 17A:
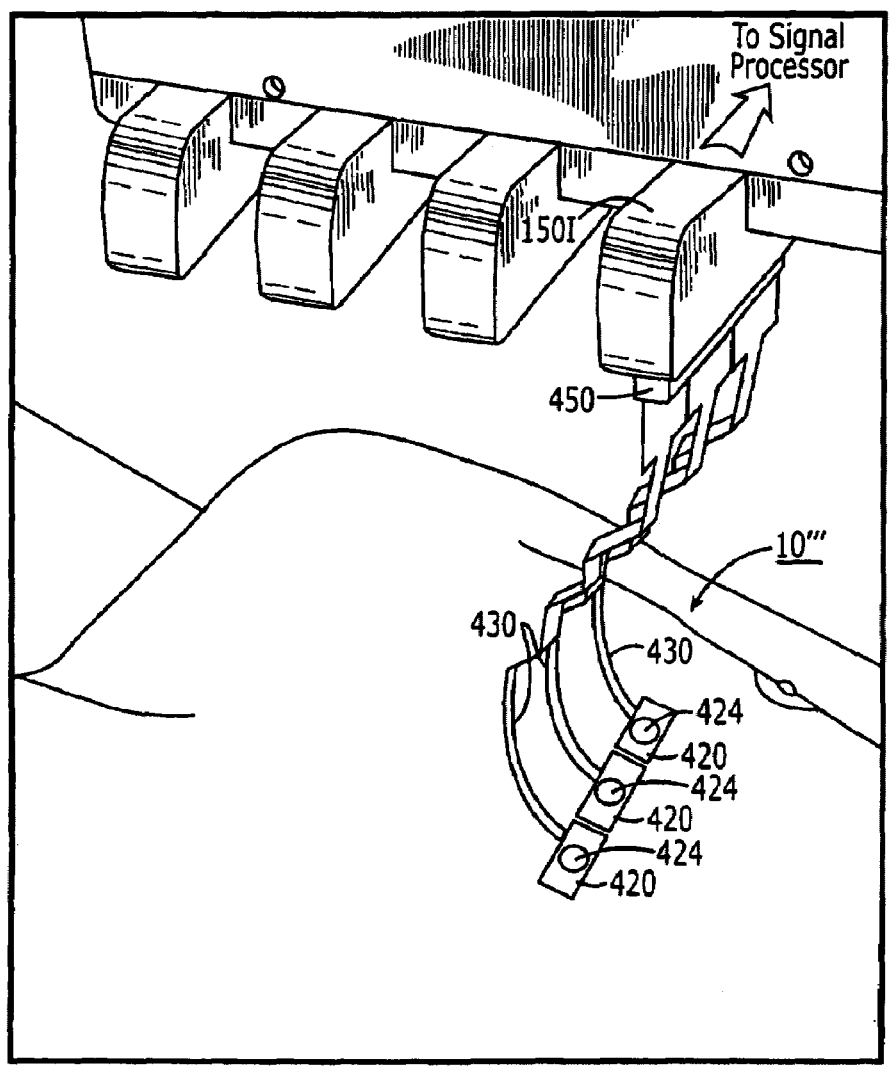
FIG. 17A is a photographic image of a side perspective view of an alternate sensor array configuration according to the present invention, the sensor array shown in position on a subject.
Figure 17B:
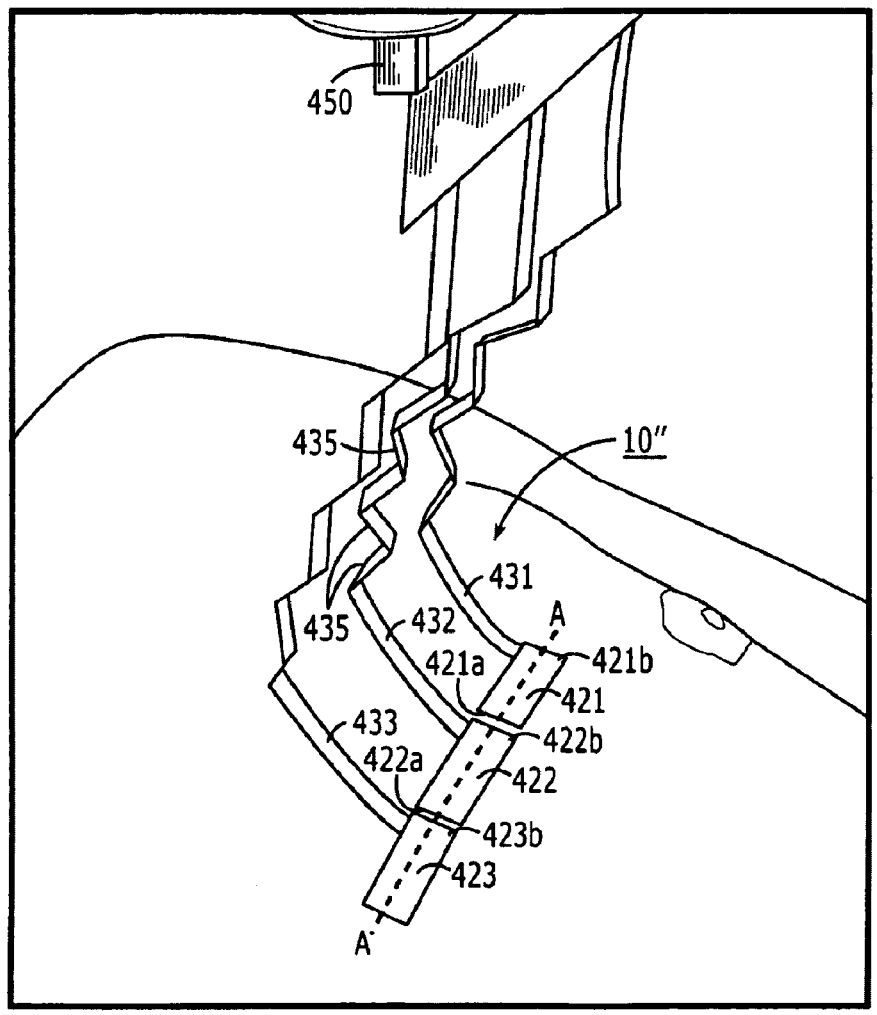
FIG. 17B is an enlarged photograph of the sensor array of FIG. 17A.

FIGS. 17A and 17B illustrate yet another preferred embodiment of an accordion pleated sensor array 10''' which can advantageously minimize mechanical vibration and cross-talk between sensor elements 421, 422, 423 and their associated transmission lines 431, 432, 433 while also providing a mechanical filter (to reject compression energy and allow selective acoustic response as discussed above) according to the present invention. This low profile acoustic accordion array is also configured to selectively respond to shear waves while rejecting compression wave energy in the frequency range of interest. As shown, this sensor array 10''' includes multiple discrete or unitized sensors 420 and corresponding individual transmission lines 430 which are electrically connected at a primary connector 450 and into the signal processor operating system 1501. As shown in FIG. 17B, the sensor array 10''' preferably includes three sensor elements 421, 422, 423 with corresponding transmission lines 431, 432, 433. The separate transmission lines 431, 432, 433 can substantially isolate each element and respective transmission line to thereby minimize the cross talk between adjacent sensor elements.

As is also shown in FIG. 17B, the transmission lines 431, 432, 433 are preferably folded or formed with a series of undulations 435 along the length of the transmission path (the transmission path extending between the sensor element 420 to the primary connector 450). Although shown as formed with accordion type "sharp" creased or crimped edges ("pleats"), it will be appreciated by one of skill in the art that other mechanical damping configurations may also be used. For example, but not limited to, the transmission line can be formed with a series of sinusoidal curves or waves or folds formed along a portion of its length, or formed with alternating material widths (e.g., thin to wide, wide to thin), or a combination of fold or curve patterns, interposed extra material or alternating material composition, weight, and the like. As used herein, the term "undulating" includes the above mechanical damping configurations.

FIGS. 17A and 17B illustrate a preferred sensor array 10''' alignment.

As shown, in position on a subject, the sensor array 10''' positions the sensor pads 421, 422, 423 such that the discrete sensor pads are configured as an array 10''' with a plurality of unitized, separated, or discrete sensors; that is, the sensors 421, 422, 423 and corresponding transmission lines 431, 432, 433 are configured as discrete aligned segments in the array, i.e., they have "unitized separation". As shown, the rear of the sensor pad 423b of the most distal sensor 423 (the sensor positioned closest to the center of the subject's chest) is proximate to the front 422a of the next adjacent sensor pad 422. The rear of that sensor pad 422b is positioned proximate to the front 421a of the next sensor pad 421. Further preferably, as shown, the sensor pads 421, 422, 423 are positioned such that they are substantially linear arranged and symmetrically extend relative to a horizontal or lateral alignment axis A—A. Further, it is preferred that each of the sensor pads is conformal to the underlying skin and the transmission lines are sized and configured such each is spatially separated from the others (i.e., non-contacting with the others).

The transmission line 430 preferably longitudinally extends off one end portion of the sensor pad (shown as the rear portion) 423b, 422b, 421b. Preferably, the sensor array 10''' is configured and sized such that the transmission line for each sensor 430 extends off the sensor pad in a manner that, when connected to the system connector 450 and securely attached to the surface of the patient, the transmission line 430 defines a concave contour along a portion of its length when viewed from the side. That is, as shown by FIGS. 17A and 17B, the length of the transmission line 430 is such that it is sufficiently long when in position so as to provide a suitable amount of slack to prevent tensioning of the transmission line when the primary connector 450 is connected to the signal processing input port 1501. In addition, as shown, the sensor array 10''' is configured such that the array includes three discrete sensors 420, and each sensor 420, sensor pad 421–423, and associated transmission line 430 is a substantial mirror image of the other sensors, sensor pads, and transmission lines. However, the sensor array 10''' can include alternative numbers of sensors such as 2, 4, 5 or more. In addition, the system can employ several of the multi-element sensor arrays 10''' (such as four) of the tri-sensor discrete element sensor array 10''' (not shown). This plurality of three element sensor arrays 10''' can reduce the number of patient interconnections undertaken by a technician at patient application in order to prepare the equipment for use, while still allowing twelve individual sensor pad elements to be used for more precise acoustic detection on a patient.

FIG. 17A also illustrates a reflector 424 positioned on each of the sensor elements 420 to facilitate the detection system's photogrammetric recognition of the positional alignment of the sensor elements 420 when on the body. The reflector 424 can be applied by various means such as via reflective paint or by attaching reflective tape to the external (exposed) surface of the sensor element 420. See e.g., co-pending and co-assigned U.S. patent application identified by 09/828,565, to Van Horn, entitled "Methods, Systems, and Computer Program Products for Photogrammetric Sensor Position Estimation." The contents of this disclosure are hereby incorporated by reference as if recited in full herein.

Figure 18A:
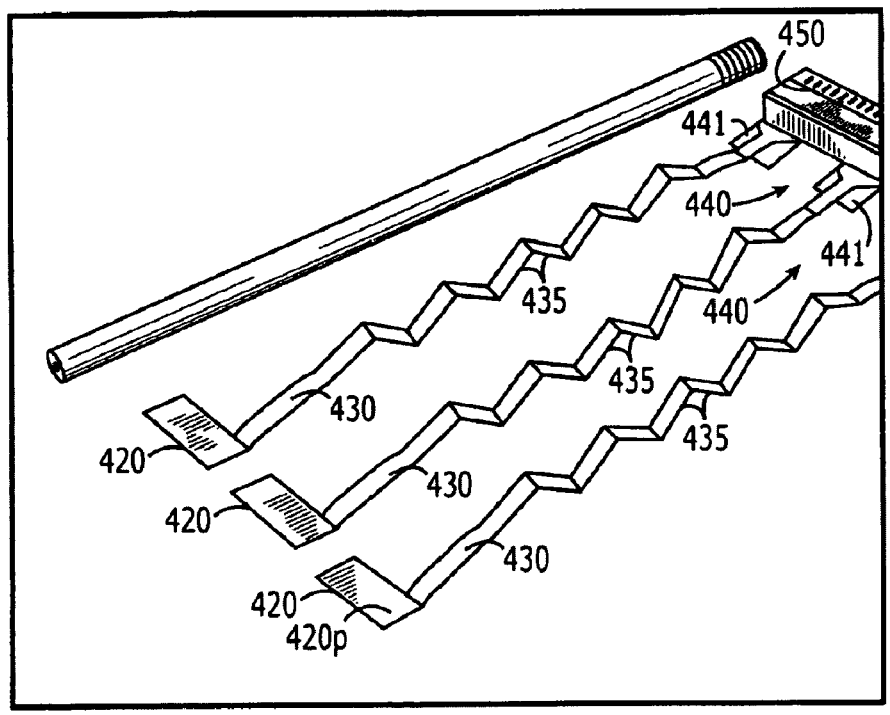
FIGS. 18A and 18B are photographic images of a side perspective view of the sensor array of FIG. 17A.

Referring now to FIG. 18A, the sensor array 10''' is shown in a pre-use position (not positioned on a subject). Each sensor 420 includes a sensor pad 420p and a termination end 440. The termination end of the sensor 440 is connected to the primary connector 450. In a preferred embodiment, a mechanical termination stiffener 441 is applied over the termination ends 440 adjacent the primary connector 450 to help stiffen and support the relatively thin ends of the sensors 420. Preferably, the termination stiffener is formed of a non-conducting material such as a transparent film or the like. Suitable materials include polyester and/or polystyrene and the like. Also preferably, each sensor 420 has a discrete or unitized termination stiffener 441 which is spatially and mechanically separate from the others to help isolate each of the signal paths from the others. The termination stiffener helps provide sufficient structure for the relatively thin flexible PVDF body 420b (FIG. 20A) onto which the connector or end terminations can be attached. Of course, alternate structural enhancing means can also be used as will be appreciated by those of skill in the art.

Figure 18B:
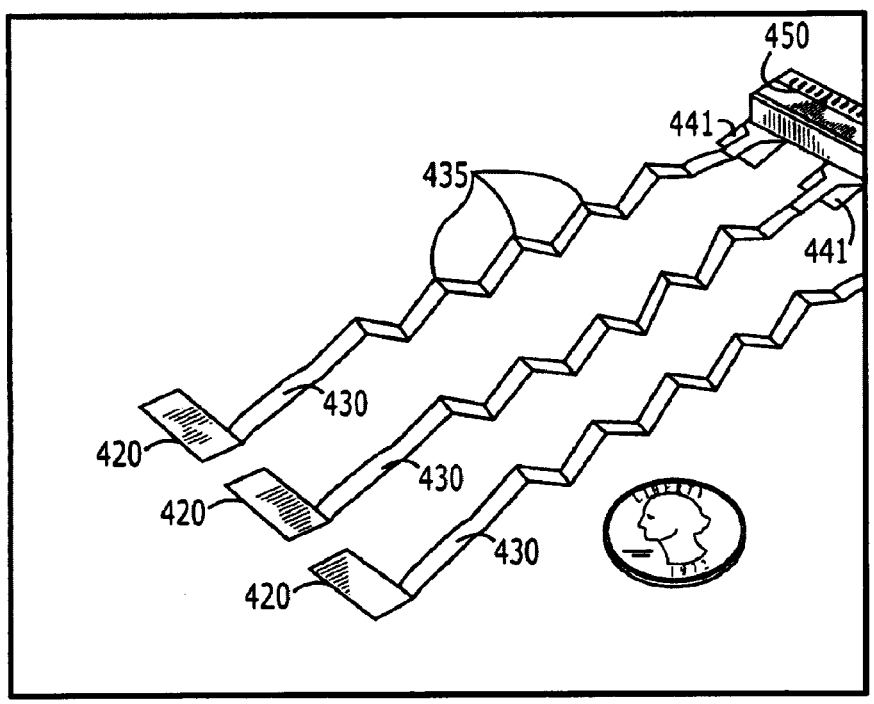

As shown in FIGS. 18A and 18B, the transmission lines 430 each include a plurality of undulations or pleats 435 formed along the length thereof (typically under about 23 cm). Preferably, each transmission line 430 is configured the same as the others. In a preferred embodiment, as shown, each transmission line 430 preferably includes at least four undulations or pleats 435 serially formed in continuous repeating (non-interrupted) fashion along a major portion of the length thereof. Of course, as will be appreciated by one of skill in the art, the number of pleats, the shape, and the pattern or configuration of same can be alternatively arranged. The undulations or pleats 435 positioned along the transmission lines 430 help to isolate the transmission paths so as to minimize the sensor array's 10''' reaction to unwanted acoustic inputs between adjacent elements or lines or even from vibration from a computer or processor or data system connected to the array for receiving the data signals associated with the flexure responsive generated signals. In another preferred embodiment, the pleats 435 or undulations begin substantially immediately after the sensor pad 420*p* and extend continuously about every 0.5 inches or 1.25 cm (0.5 inches or 1.25 cm edge to edge) along the length of the transmission line 430 until the termination end of the sensor 440.

It is also preferred that the electrical lead lengths of the transmission lines 430 and each of the sensor pads 420*p* are maintained as a constant size and length to allow for the differential sensing capability such as discussed under the section describing the other sensor array configuration above.

Figure 19A:
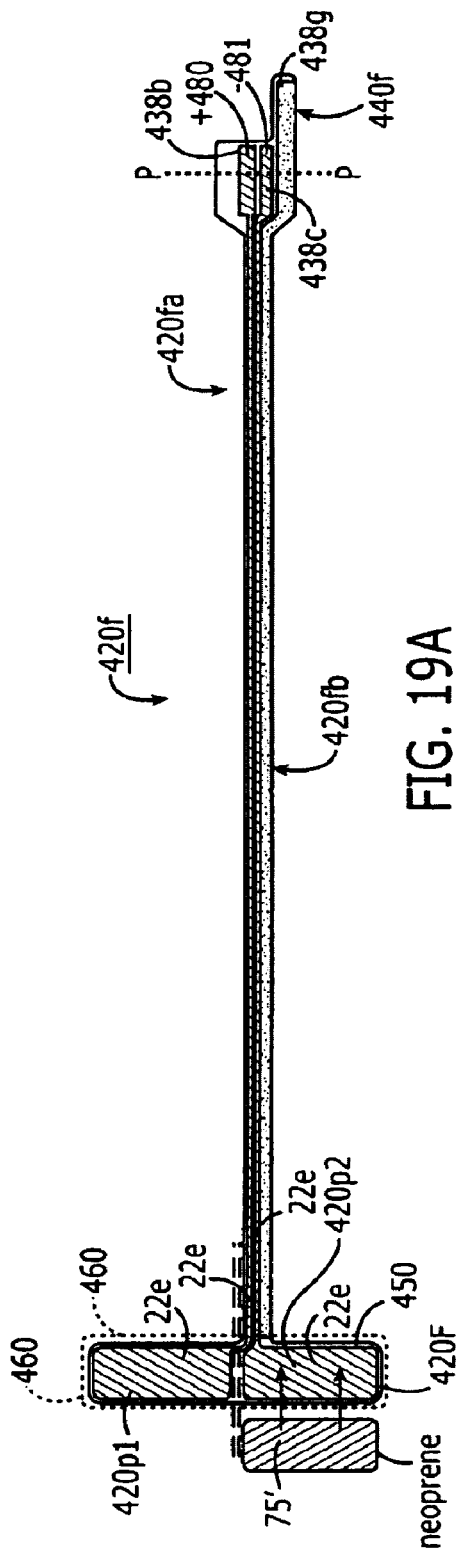
FIG. 19A is a top view of a preferred embodiment of a sensor film body configuration suitable for forming the sensor element for the sensor array shown in FIG. 17A.

Referring now to FIGS. 19A and 20A, a preferred embodiment of a sensor body 420*b* is shown. Similar to the embodiment shown in FIG. 8A, the sensor body 420*b* includes a thin layer of piezoelectric film 420*f* ("PVDF") having opposing first and second major surfaces 420*f$_a$*, 420*f$_b$*. The first major surface 420*f$_a$* of the film includes an active metallized electrode surface 22*e* defining the opposing sensor pad regions 420*p*1, 420*p*2. The first major surface 420*f$_a$* also includes the separate electrical traces 480, 481. Preferably, the electrical traces outside the electrode regions are inactive, for example, by the trace regions not being initially polarized, or depolarized such that they act to carry or transmit flexure signal generated by the electrode sensing regions.

Figure 19B:
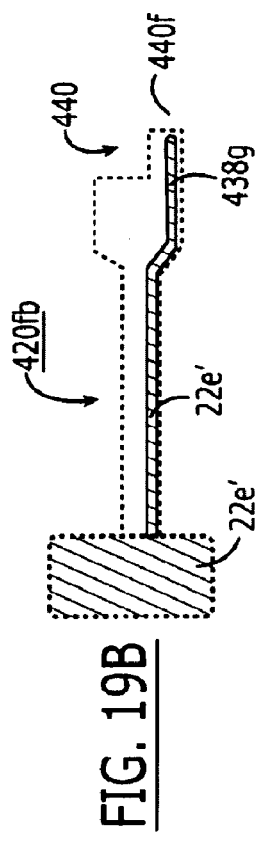
FIG. 19B is a bottom view of the sensor film body of FIG. 19A.

The second major surface 420*f$_b$* of the PVDF film layer 420*f* (the surface underlying the exposed surface shown in FIG. 19A) is formed from a conductive trace such as a conductive ink (but of course other methods for disposing a conductive trace can also be used such as those described hereinabove). As shown in FIG. 19B, the second major surface 420*f$_b$* is preferably configured to provide a continuous conductive active surface pattern 22*e'* which includes the upper portion of the "T" defined by the two pad portions of the sensor body 420*p*1, 420*p*2. The second major surface 420*f$_b$* also includes a trace 438*g* positioned along one side of the (PVDF film). This third transmission line or trace 438*g* acts as a ground signal path or line.

In a preferred embodiment as shown in FIG. 19B, the trace 438*g* is preferably configured to extend a greater distance on the termination end of the sensor 440 and thus form the long finger portion 440*f* of the termination end of the sensor. This additional length allows this portion of the sensor to be folded over to the other side of the sensor to align the ground signal line 438*g* with the signal transmission lines 438*b*, 438*c* for each of the electrodes 450, 460. As shown in FIGS. 21B and 22, this termination configuration provides a four point termination, one each associated with the electric shield "ground" 438*a*, the PVDF film layer traces 438*b*, 438*c*, and the folded 438*g* ground trace. The four-point termination connection for the primary connector 450 is thus configured on a single common connection surface.

The PVDF film layer 420*f* defines the acoustic sensor signal paths 480, 481, and ground signal path 438*g* for each of the sensor pads or electrodes 450, 460, including the active portion of the sensor pad 420*p*1, 420*p*2 and the associated transmission or signal paths 438*b*, 438*c*, 438*g*. Similar to the operation of the differential sensor 63 explained for FIGS. 13 and 13A, the PVDF film 420*f* is preferably configured to provide opposing sensor pads 420*p*1, 420*p*2 which act as electrodes 450, 460 having opposing polarities. As shown in FIG. 20B, the negative and positive polarity associated with the upper and lower electrodes 450, 460 provide the differential configuration for the flexure induced voltages $v_1$, $v_2$. Of course, as note for the above-described embodiment, the polarities can also be reversed, but the sensor region is preferably configured with opposing polarities for the sensor pad in order to provide the differential based operational sensing configuration. In any event, as shown, the PVDF film layer 420*f* is configured to provide an upper electrode surface and a lower electrode surface 450, 460, respectively (the lower electrode surface and the surface shown in FIG. 19A disposed on the patient such that these surfaces face the skin of the patient).

Preferably, as shown in FIG. 20A, in order to form the sensor assembly 420, a layer of nonconductive material (such as polyester film) 499 is attached to or applied to overlie substantially the entire length of both sides of the PVDF film layer 420*f* along the linear transmission line 430 or trace portion of the sensor body 420*b* (excluding both sides of the sensor pads 420*p*1, 420*p*2 or upper portion of the "T" region of the sensor body). Preferably, as is also shown, the polyester film layers 499 end a distance away from the termination end of the sensor 440—substantially along a line shown by P—P in FIG. 19A and FIG. 21B. A single sided or double sided adhesive-backed polyester tape can be conveniently used to attach the polyester layers to the respective PVDF film surface 420*f$_a$*, 420*f$_b$*. Of course, other adhesive or attachment means can also be used as will be appreciated by one of skill in the art.

The sensor body 420*b* also includes a resilient core 75' which is applied to one side of the sensor pad region of the sensor body 420*b* as shown by the arrow associated with the core element 75' drawn in dotted line in FIG. 19A. FIG. 20A also shows the preferred assembly position of the core 75' relative to the sensor pad 420*p*2 region of the sensor body 420*b*. In position, the core 75' is positioned to overlie and attach to the sensor pad 420*p*2 (such as via an adhesive). As shown in FIG. 20A in double-dotted line, to form the flexure-responsive sensor element 421–423, the PVDF film sensor pad 420*p*1 is folded over the central core layer 75' to overlie the opposing PVDF film sensor pad 420*p*2 as shown in cross section in FIG. 20B. The folded configuration of the sensor 420 (that is preferably only the sensor pad region is folded) is shown in FIGS. 18A and 18B.

As is also shown in FIG. 20A, in this embodiment, first and second layers of conductive shielding material layers 501, 502 are attached to the sensor body 420*b*. In a preferred embodiment, the shielding material layers are metallized film, and more preferably a thin sheet of MYLAR® film. The conductive shielding material layers 501, 502 help to shield the sensor 420 to minimize the introduction of electromagnetic interference into the sensor signal paths. As shown in FIG. 20A, the shielding material layers 501, 502 are sized and configured so that they do not contact along the sensor pad region of the sensor, ie., the perimeter edges of the sensor pad are not enclosed by the shielding material layers 501, 502 when the PVDF film sensor pads are aligned over the core 75'.

As shown in FIG. 20A, the first shielding layer 501 linearly extends from the upper neck portion of the sensor body to an end portion which is adjacent the termination end of the sensor 440. In this embodiment, the first shielding layer does not extend to cover the PVDF sensor pad regions 420*p*1, 420*p*2. As is also shown, the first shielding layer 501 ends at substantially the same position as the polyester layer 499 but also includes a termination protrusion end 438a which longitudinally extends a further distance to align with the active signal transmission lines 438b, 438c.

Figure 21A:
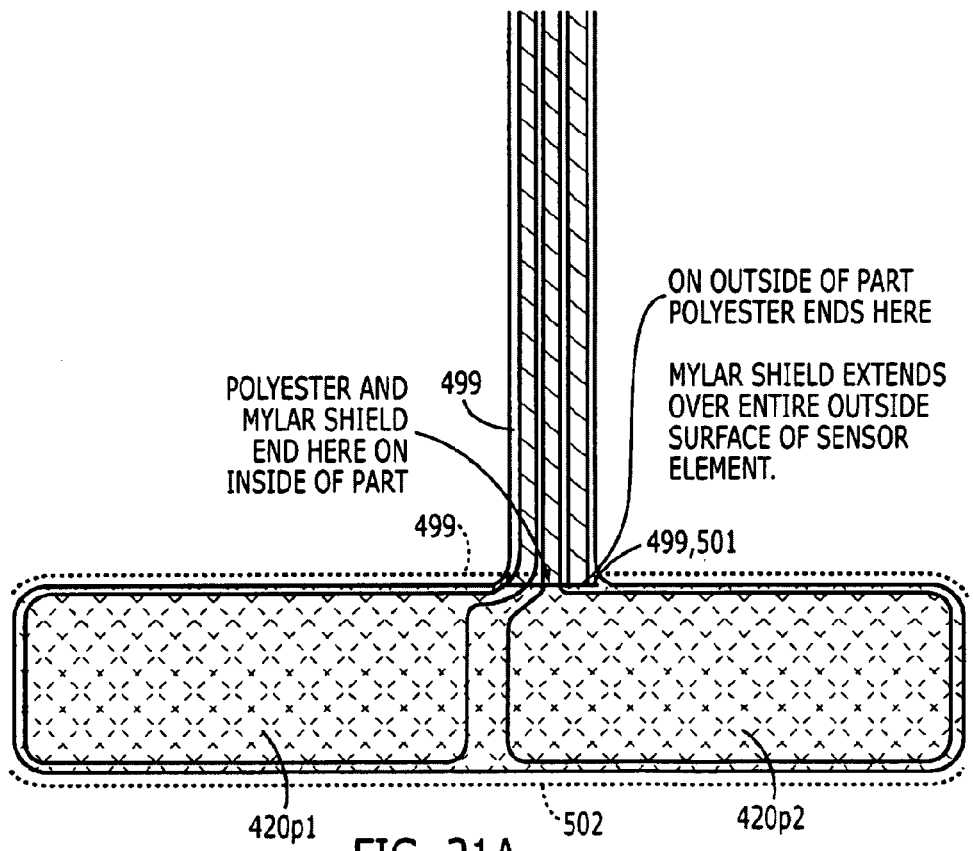
FIG. 21A is a partial top view of a sensor film body and polyester layer according to a preferred embodiment of the present invention.
Figure 22:
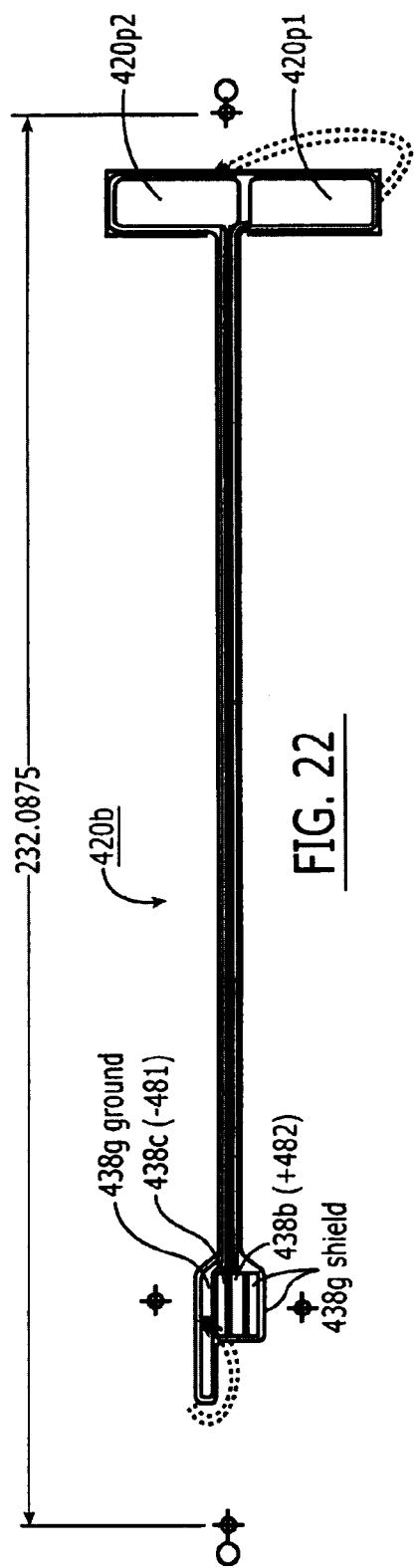
FIG. 22 is a top view of a sensor body according to the present invention, the view illustrating four end terminations formed by a preferred embodiment of the present invention.

FIG. 21A shows the preferred end point for the non-conducting layers 499 and the upper shielding layer 501. As shown, the material extends adjacent but below the sensor pad regions 420p1, 420p2. FIG. 21B shows the outer shielding material layer 501 positioned on the PVDF film layer 420f. As noted, the shielding layer 501 and the intermediately positioned polyester layer 499 end at a common termination line P—P for a major portion of the outer shielding material layer 501. This configuration allows electrical access for the signal lines 438b, 438c. This configuration also allows for electrical engagement with the ground path 438g when it is folded up to contact the shielding material layer 501.

As shown in FIG. 20A, the second or opposing outer shielding layer 502 is configured and sized to substantially conform to the shape and size of the unfolded PVDF film layer 420f. As such, it includes a "T" shaped body of which the upper portion is preferably folded along with the sensor pad 420p1. When folded, the second shielding layer 502 provides a continuous electric shield for the exposed major surfaces of the sensor pad 420p and also preferably ends into or contacts the upper portion of the first shielding layer 501a at a lower edge 502a. Accordingly, the two opposing shielding layers 501, 502 provide a contiguous shield for the sensor 420 as shown in FIG. 17A while the insulating polyester film layer maintains the electrical integrity of the internally disposed signal paths 438b, 438c. Similar to the first shielding layer 501, the second shielding layer 502 also includes a longitudinally extending protrusion portion 438a' positioned to overlie the first protrusion 438a with the PVDF film layer 420f disposed therebetween. Upon termination into the connector, the protrusion portions 438a, 438a' provide the electrical continuity for the shield layers 501, 502.

FIG. 22 illustrates the electrical signal paths 438a, 438b, 438c, and 438g formed onto the sensor body 420b. The live signal paths with opposing polarity are 438b and 438c, while the ground is provided by 438g and the shield by 438a, 438a'.

Advantageously, as shown in FIG. 20b, the electrode configuration 450, 460 is such that the sensor 420 acts like a differential amplifier 63' as discussed for the embodiment described above. In operation, the sensor 420 takes the voltage differential of the two response voltages $v_1$, $v_2$ to generate a signal response which has an increased voltage value (approximately doubled value) and, thus, can provide improved SNR performance. Further, for non-flexure sensor excitation, the voltage polarities are such that the signal responses from each layer 450, 460 cancel each other, minimizing signal output for non-flexure excitations.

Preferably, the sensor component materials such as for the core are selected and configured as described for the first embodiment described herein.

Figure 23:
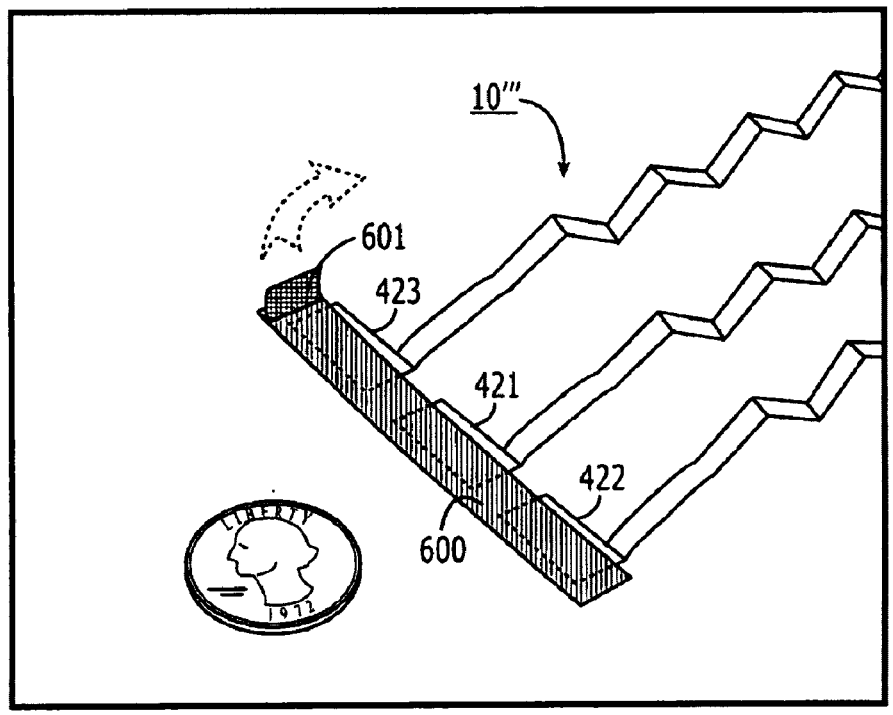
FIG. 23 is an enlarged photographic image of the sensor end of the sensor array of FIG. 17A having a detachable carrier member according to the present invention.

As shown in FIG. 23, the sensor array 10''' preferably includes a structural support or carrier member 600 which is positioned over the exposed side of the plurality of sensors 420 (the side away from the patient when in operable position). The carrier member 600 is release-ably secured to each of the plurality of sensors 421, 422, 423. Thus, the carrier member 600 is used to maintain the sensor elements 421, 422, 423 in a predetermined alignment so that an operator or technician can remove the sensor array from a shipping package, attach the discrete sensor elements 421, 422, 423 onto the patient, and strip the carrier member 600 away, conveniently providing unitized installation for discrete sensors. The underside of the sensor elements 421, 422, 423 preferably includes a layer of adhesive which is configured to securely attach the sensor's in position on a patient during use as described for the first embodiment above (of course, the adhesive can be directly applied to the patient instead). The carrier member 600 conveniently allows the technician or operator to easily position the discrete individual sensor elements 421, 422, 423 onto the patient while maintaining the preferred alignment positional relationship therebetween. Thus, the carrier member 600 is configured to be temporarily attached to the sensor elements 421, 422, 423 (only during shipping and patient application, i.e., attached during the time period prior to sensor operation). Advantageously, the carrier member 600 can limit the number of installation steps the operator must take to prepare the patient for acoustic evaluation. Further, the carrier member 600 is configured to release or detach from the sensors 421, 422, 423 once the sensors are secured to a patient. Of course, this carrier member can also be used with other flexible low profile sensor arrays to help facilitate the positional and structural integrity while applying same to the patient.

This disengagement is preferably accomplished by disengaging an edge portion of the carrier such as an exposed tab 601 and pulling the carrier member 600 away from the sensor elements 421, 422, 423 without disturbing the installed position of the sensors on the patient. Advantageously, the carrier member 600 provides the installation convenience of structurally related sensors while also allowing the structural isolation of the sensors during operation.

Figure 27:
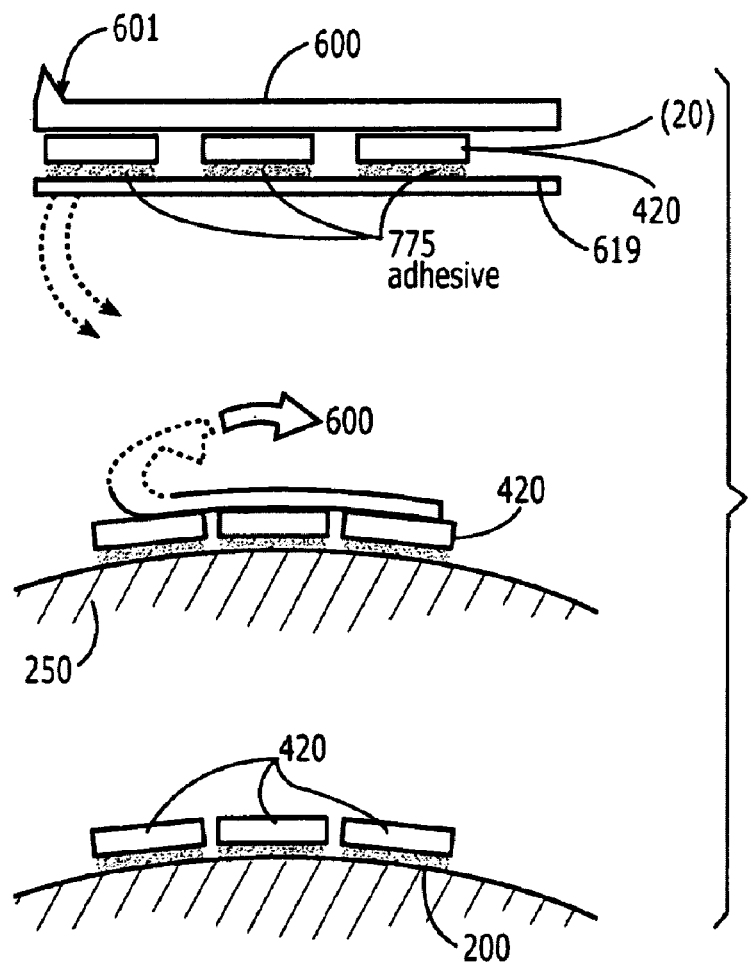
FIG. 27 schematically illustrates an operational shipping and application method according to the present invention.

FIG. 27 schematically illustrates the preferred product configuration with the releasable carrier member 600. Step 1 includes a first carrier member 600 and a second carrier member 619 used during transport or shipment to a use facility (step 1). As shown, the second carrier member is an easily releasable (low peel strength) tape or the like which is used to protect and maintain the patient-adhesive material intact during shipment. Step 1 also shows that prior to use, the second carrier member is pulled away and released exposing the bottom of the sensor elements and the adhesive thereon. Step 2 illustrates that, once the sensor elements are secured to the patient, the top carrier member 600 can be pulled away leaving the sensor elements exposed. Thus, the top carrier member 600 preferably has a peel strength which is less than the bond strength of the adhesive/patient attachment. The top surface of the sensor elements can also include discrete masses or reflectors as will be discussed further below. Step 3 illustrates the positional alignment of the sensor elements 420 provided by the fixed structural relationship via the top carrier member 600 during positioning onto a patient. Thus, conveniently, once the top carrier member 600 is stripped away, the sensor elements 420 are in position and ready for acoustic operation. The carrier member 600 is particularly helpful for discrete element sensor arrays 420, but the present invention is not limited thereto, and can of course, be employed with the strip array 10 embodiment described herein.

Figure 24A:
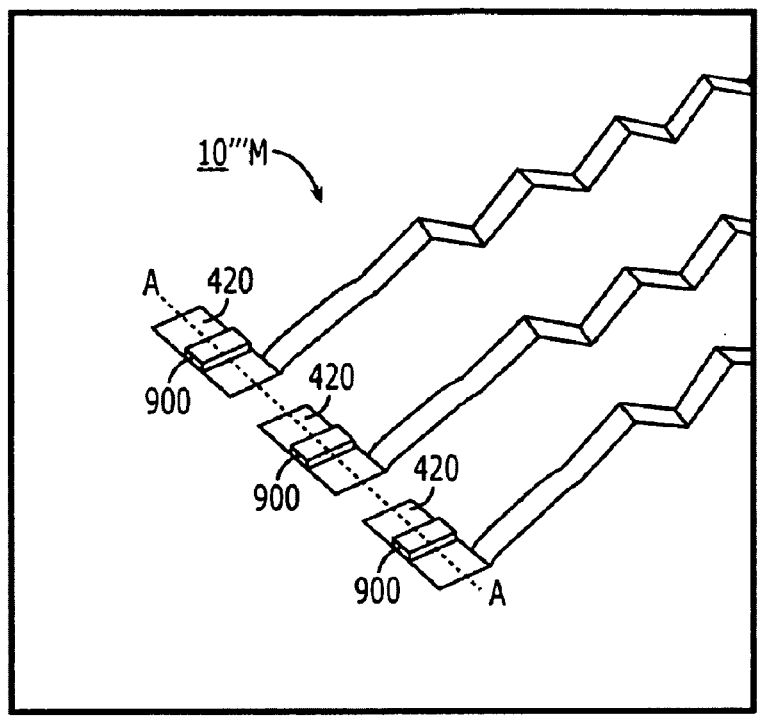
FIGS. 24A–E illustrate the use of discrete masses with flexure responsive sensors according to the present invention.

Another preferred embodiment of the present invention includes a sensor array 10'''M as shown in FIG. 24A. In this embodiment, at least one discrete mass 900 or external flex stiffener 910 is added to the upper (exposed when on a patient) surface of each sensor element 420. This configuration can modify the flexural response of the sensor element 420 and may improve the coupling of the sensor. Preferably, the discrete mass 900 or external stiffener 910 extends across at least a portion of the short dimension of the sensor element. It is also preferred that the mass (or stiffener) be sized and configured on the sensor element 420 such that it is locally discrete as opposed to distributed (distributed meaning extending continuously across the long dimension of the sensor element).

In a preferred embodiment, as shown in FIG. 24A, a centrally positioned discrete mass is positioned on each sensor element 420. Preferably, the mass is formed from a high-density material such as a tungsten alloy, lead, or other heavy metal. A suitable discrete mass 900 weighs about 3–6 grams, and more preferably about 4.5–5 grams. Typical dimensions of the discrete mass is about 0.2×0.2×0.42 inches (or about a 5 mm length across the short dimension of the sensor pad). Examples of discrete external stiffeners include a layer of material having a different (more rigid) stiffness as compared to the PVDF layers or the core.

Figure 24B:
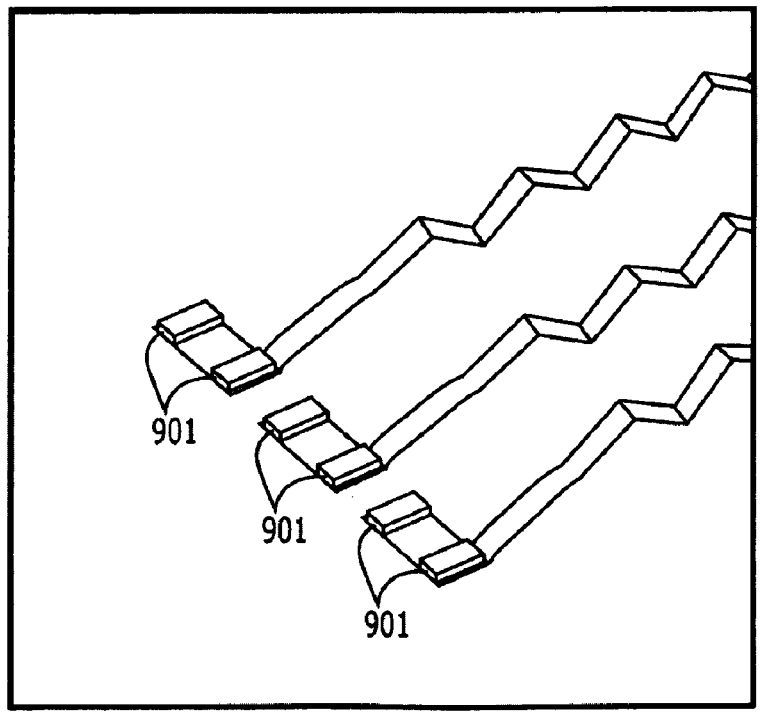
Figure 24C:
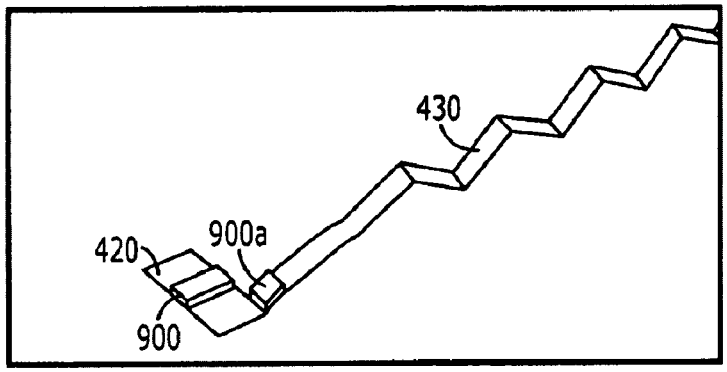
Figure 24D:
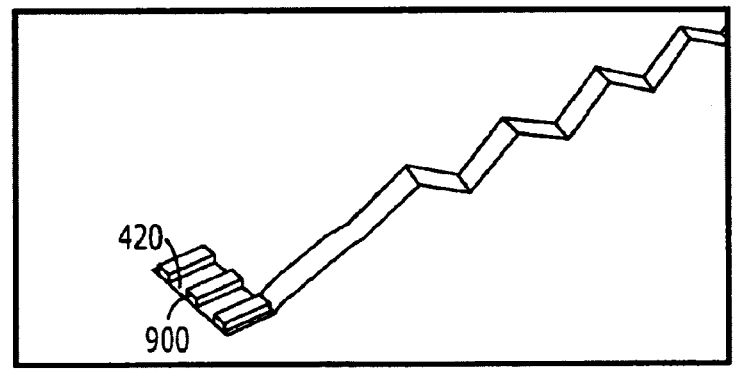
Figure 24E:
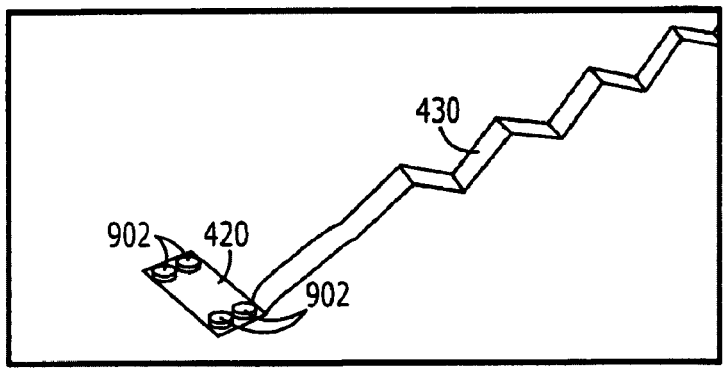
Figure 25A:
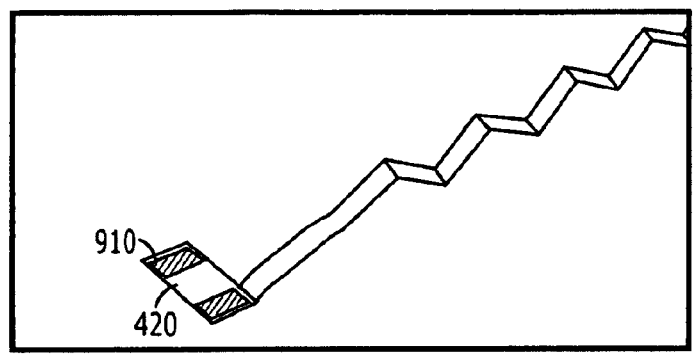
FIGS. 25A–C show the use of external stiffeners for flexure responsive sensor elements according to the present invention.
Figure 25B:
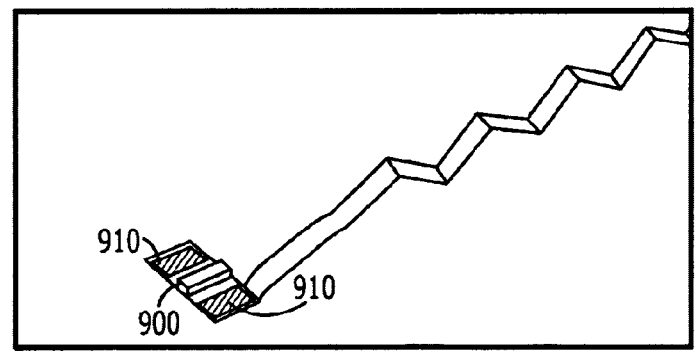
Figure 25C:
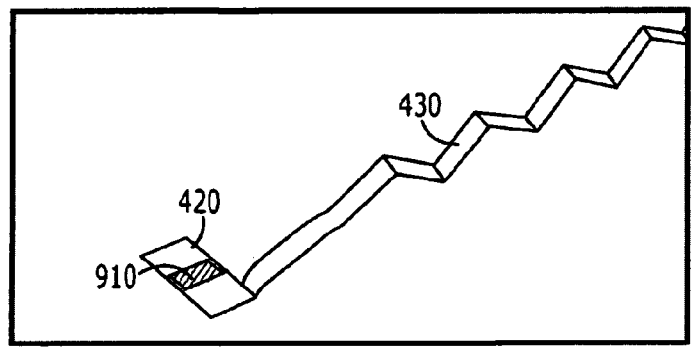

FIGS. 24A–E, 25A–C, and FIG. 26 illustrate exemplary discrete mass and stiffener configurations according to the present invention. FIG. 24B illustrates a plurality of discrete masses 901 positioned on opposing ends of the sensor elements 420. FIG. 26 illustrates a discrete mass 900 positioned on the strip array 10. FIG. 24C illustrates a discrete mass 900 positioned on the sensor element 420 and a discrete mass 900 and a second discrete mass 900a positioned on the transmission path 430. FIG. 24D illustrates a plurality of discrete masses 900 positioned onto the sensor pad 420. FIG. 24E shows a plurality of alternately configured discrete elements 902 positioned on the sensor element 420. FIG. 25A illustrates a pair of opposing external stiffeners 910 positioned onto the sensor element 420 while FIG. 25C illustrates a single center stiffener 910. FIG. 25B shows that the stiffener 910 can be combined with a discrete mass 900.

The reflectors (424, FIG. 19A) or a reflective material can also be conveniently applied to the exposed surface of the stiffener 910 or discrete mass 900 to facilitate system positional operational alignment as discussed above.

Additionally, the stiffness of the sensor element 20, 420 can be adjusted by selecting the core materials to provide a different more stiff resilience at one or more regions in the pad such that the stiffer regions extend in at least one region across at least a portion of the short side of the sensor.

Fabrication

As shown, in FIGS. 1A and 1B, in a preferred embodiment, the sensor array 10 is fabricated as a unitary body. That is, unlike conventional sensors, there is no requirement to assemble discrete sensor elements onto an underlying electrical ribbon. Preferably, at least the frame 15 and sensor elements 20 are configured as a unitary body, and more preferably, the sensor array itself 10 is an entirely unitary body (i.e., a single piece construction comprising multiple layers but no discrete components excepting an electrical interface connector (not shown) which is adapted to be engaged with the electrical terminations 40).

For the embodiment shown in FIG. 17A, it is preferred that the core 75' be extruded, molded, formed, or cut, and that after the electric shield layer and other layers are positioned (and the sensor pad folded), the undulations be formed by mechanically crimping the assembled sensor at desired spacings along its length. Of course, other crimping means or forming means such as specialized tooling can also be used to configure the undulations onto the sensor body as will be appreciated by those of skill in the art.

Figure 16:
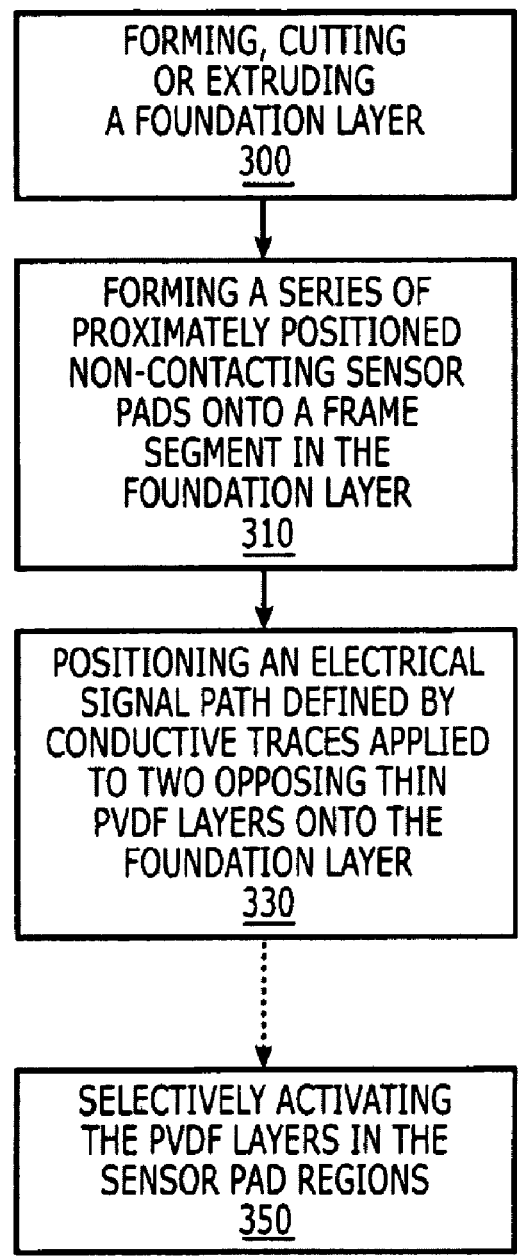
FIGS. 16 and 16A are block diagrams of preferred methods of forming a strip sensor array according to the present invention.

FIG. 16 shows a block diagram describing a preferred method of fabricating a low profile sensor having two separate PVDF layers according to the first described embodiment. After the foundation or core is formed (i.e., such as cut or extruded), the outer layers 50, 60 are attached thereto to form the strip sensor (Block 300). The foundation layer is cut so that a series of proximately located and non-contacting pads are formed onto a frame segment in the foundation layer (Block 310). An electrical signal path is positioned onto each of the outer layers (PVDF film) which is then secured to the foundation layer (Block 330).

Optionally, the PVDF film may be selectively activated, ie., only selected regions such as the sensor pad regions are actively polarized. Alternatively, selected portions of the PVDF film may be substantially deactivated by applying heat thereto (Block 350). As will be appreciated by those of skill in the art, in order to appreciably enhance the piezoelectric effect in the PVDF material, the material is typically exposed to an appropriate electrical poling potential across the thickness of the film for an extended period of time. As used herein the term "selectively activating" or "selectively polarizing" thus means exposing selected regions of the PVDF material to an electrical poling potential to enhance the piezoelectric effect in the film. Thus, during manufacturing, exposing only the sensor pad regions and not the rails can minimize the "active" nature of the rails and/or non-sensing areas of the PVDF film thereby providing substantially "non-active" regions. In addition, as noted above, the entire sensor can be subjected to the electrical poling potential, and then the rails can be "de-poled" such as by heating. Alternately, of course, "selective polarization or activation" is not required. For example, the entire PVDF film employed in the sensor can remain piezoelectrically enhanced or "activated".

Figure 16A:
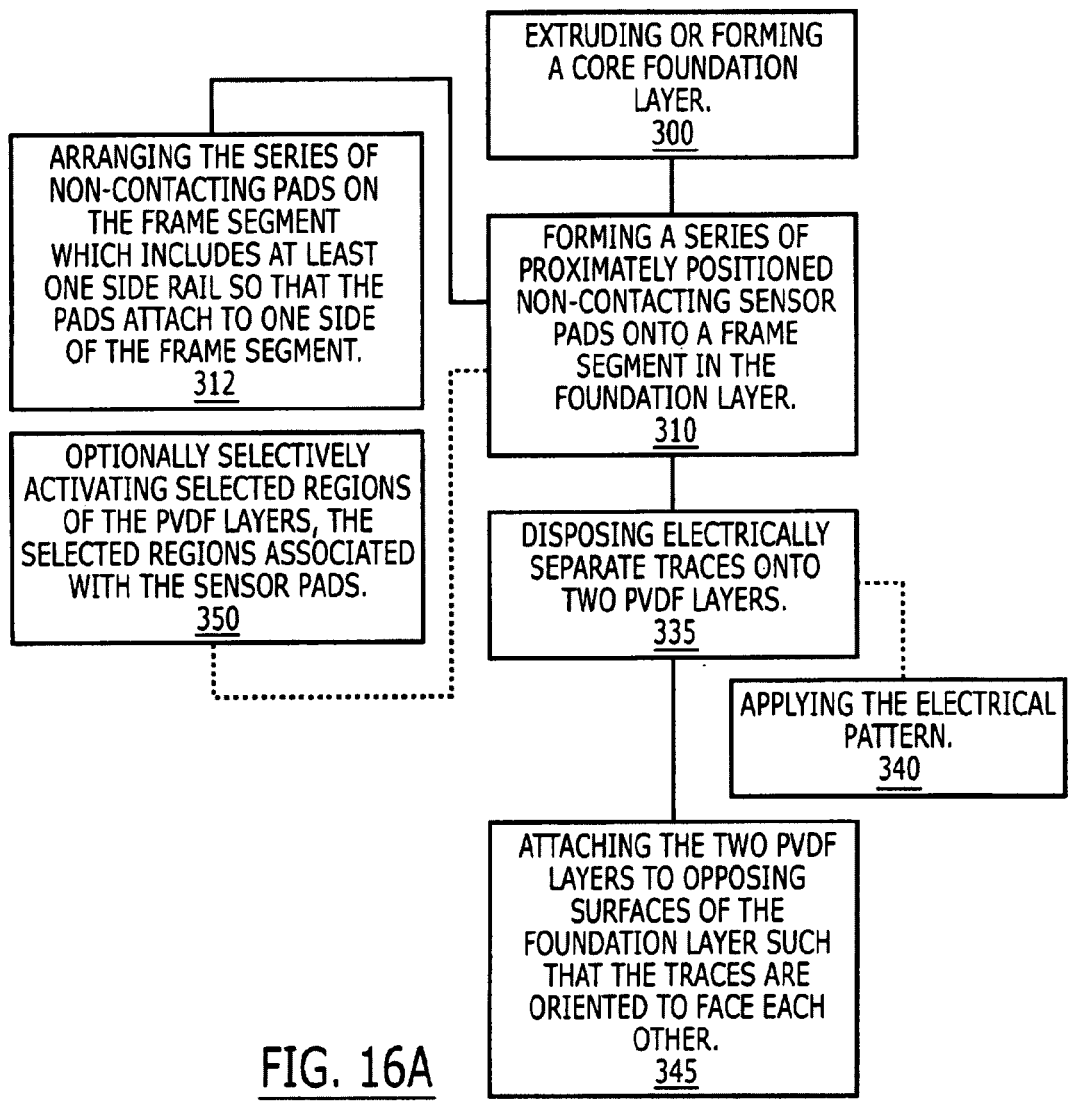

FIG. 16A illustrates additional preferred method steps. As shown, the frame segment is formed such that it includes a pair of longitudinal sides and the series of non-contacting pads are arranged to attach to one side of the frame segment (Block 312). Preferably, a pattern defining a plurality of electrically separate external traces are disposed onto a surface of each of two PVDF layers (defining a corresponding top and bottom electrical trace which is associated with each of the longitudinally extending opposing sides and the sensor pads) (Block 335). Also preferably, as shown by (Block 340), the disposing step is performed by applying a conductive layer with a trace pattern such as via conductive ink and the two PVDF layers are attached to the foundation layer such that the signal traces face each other and contact the foundation layer. (Block 345).

Preferably, for extruding the core 75 or 75', or for the foundation-forming step, a neoprene core material is inserted into a die. As discussed above, the PVDF material is preferably introduced onto the core layer 75 (75') such that a first outer layer 50 has a first polarity and a second outer layer 60 positioned contacting the core 75 opposing the first outer layer 50 has a second polarity, the second polarity being the reverse of the first polarity. Preferably, the fabrication process introduces the core material into the forming, cutting or extruding machine such that it terminates in the finished extruded product at a longitudinal distance away from the frame along the foundation layer (100, FIG. 6). The frame pattern is then cut to form the foundation layer. (which includes the core 75 and two opposing outer layers 50, 60 as discussed above). In a preferred embodiment, the foundation layer defines a linear arrangement of a plurality of sensor pads. An electrical signal path is positioned onto the external surface of the foundation layer 100. Preferably, the electrical trace pattern is introduced onto the PVDF layer by applying a conductive ink in a silk screen pattern thereon. Preferably, a conductive electrical trace pattern is disposed onto two (preferably planar) separate surfaces of the two PVDF layers, the top outer surface and the bottom outer surface 50, 60. The electrical pattern includes a sensor pad active region 220 and linear traces 221. Further preferably, the same pattern is disposed as an external trace onto each transverse outer surface, such that the sensor array has two separate signal paths for each element 20, the signal paths separated by the core material depth or thickness. Optionally, as noted above and illustrated by Block 350, the PVDF can be selectively polarized or selected portions of the outer layers can be de-polarized. For example, as schematically shown in FIG. 6A, the frame portions which carry the linear external trace portions can be non-activated or heated to deactivate the PVDF material in that area to minimize the potential for signal excitation in this area so as to inhibit interaction or activation along the length of the array.

FIG. 20A shows a preferred method of fabricating a low profile sensor having discrete elements as shown in FIG. 17A. Generally described, a first unitary layer of PVDF film is configured with a laterally extending portion having a first width and a longitudinally extending portion having a second width. The longitudinally extending portion preferably extends from a lower edge of a center of the lateral portion, thus forming a "T" shape configuration. Electrical traces are formed onto both major surfaces of the PVDF layer. The electrical traces are formed as a rectangular shaped sensor element onto the upper or lateral portion of the "T" such that this portion defines the two separate electrode regions with opposing polarity. The electrical traces are formed onto the lower portion of the "T" to define three electrical paths. The first and second paths are formed on one major surface adjacent to one side to provide the electrical signal path for the first and second electrodes. The third path is formed on the opposite side of the PVDF layer (on the second major surface). The third path preferably includes a primary finger portion. The third path forms the electrical ground and extends along the side of the second major surface opposite the side the first and second paths are formed on the first major surface.

A resilient core (such as neoprene) is inserted onto the top surface of one of the electrode regions. Linear strips of non-conducting film is positioned to overlay the lower portion of the "T". A first electric shield material (such as MYLAR@) is positioned to overlay the lower portion of the "T" over the non-conducting (polyester) film on the side opposing the first major surface of the PVDF film (the side with the first and second electrical paths) and preferably includes a conductive finger portion. This conductive shield layer does not extend into the electrode region. On the second outer surface, a "T" shaped conductive shield layer is configured and sized to mirror the PVDF film shape. This outer conductive shield layer is positioned to overlay the second major surface of the PVDF film in the electrode region and to overlay and contact the non-conducting film in the linear transmission layer.

The laterally extending portion of the PVDF film with the outer shield thereon is folded over the neoprene core such that the first and second electrode regions are positioned opposing the other with the core in contact with each and positioned intermediate thereof. The finger of the ground strip is folded up to contact the first conductive shield material thereby providing a substantially continuous electric shield for the sensor while maintaining the electrical integrity of the electrode sensors. The transmission line is then preferably crimped at predetermined portions to create the undulations along its length. The sensor is then preferably combined with a plurality of other sensors and packaged as a sensor array. The sensor array preferably includes a carrier member which is configured to hold the sensor elements in positional alignment until the sensor elements are secured to the patient. At that point, the carrier member can readily be detached from the individual sensor elements leaving them in place (in predetermined alignment) and structurally separate and physically isolated from the others. Stated differently, the sensor array is configured with a plurality of unitized sensors held by a unitizing member, and after applying the unitized array to a patient, the unitized member is readily removed leaving the sensors secured to a patient in a predetermined alignment.

Advantageously, the instant invention can provide a low profile sensor package which can be more responsive to acoustic signals measured on the external epidermal layer (conforms to patient chest area and flexes in response to chest movement). Further, the instant invention provides a smaller array package with closely positioned separately electrically activated sensor elements thereby allowing additional sensors in a smaller region to allow a more discerning sensor measurement. Further, the sensor array can selectively respond to the shorter wavelengths for the acoustic wave input of interest particularly those associated with evaluating coronary artery disease.

It will also be appreciated that the PVDF can be selectively activated in the sensor pad region as described above (or the PVDF be deactivated in the non-sensor pad region, preferably at least along the electrical traces) for all of the embodiments described herein.

It will also be appreciated that the sensor elements 20, 420 can be alternatively configured such as but not limited to a triangle, square, circle, parallelogram, octagon, and the like. Similarly, the discrete masses 900 or external stiffeners 910 can also be configured in alternative shapes such as but not limited to a triangle, square, circle, parallelogram, octagon, and the like.

While one embodiment of the present invention has been described with respect to a frame having two sides or rails, the present invention may also take the form of a single frame or single rail member with sensors formed on one or both sides of the frame or rail or alternatively, discrete element sensors. Accordingly, the present invention should not be construed as limited to structures with a particular number of frame members or with a particular configuration of the frame but should encompass any frame structure or discrete sensor structure which allows for the differential operation of the sensor array according to the present invention.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A low profile acoustic sensor array, comprising:
a plurality of discrete aligned spaced apart conformable acoustic sensor element pads, each including an active sensing element comprising piezoelectric material, wherein each sensor element pad is conformable to a shape of an underlying structure, and wherein, in operation, the sensor element pads are configured to generate a respective electrical signal in response to flexure induced by acoustic signals; and
at least one longitudinally extending elongate strip integrally attached to at least one of the plurality of acoustic sensor pads, the elongate strip having a length with opposing first and second end portions, the elongate strip comprising at least one discrete electrical transmission path thereon, the second end portion of the elongate strip adapted to connect to an output device, wherein a respective elongate strip is configured so that the at least one integrally attached acoustic sensor element pad extends outwardly away from the primary direction of the strip, the number of discrete electrical transmission paths on the strip corresponding to the number of acoustic sensor element pads held by the strip with a respective acoustic sensor element configured to be in electrical communication with a respective electrical transmission path.

2. An acoustic sensor array according to claim 1, wherein each of said strips comprise a plurality of sensor elements, wherein each of said strips include first and second transversely opposing frame rails, wherein said opposing rails are spatially separated along a major portion of said frame length, wherein each of said sensor elements is sized and configured to extend between said sensor frame opposing rails, wherein each of said sensor elements is attached to a selected one of said frame rails, wherein the strip comprises an elongate medially located neck portion that extends longitudinally away from the frame rails, the neck portion having a first width that merges into the frame rails that span a second larger width, and wherein a respective electrical transmission path on the strip laterally extends outward from a corresponding acoustic sensor element pad then turns to extend longitudinally about the one longitudinally extending rail, then laterally turns inward a distance and extends longitudinally along the neck portion.

3. An acoustic sensor array according to claim 2, wherein said sensor elements are arranged on said frame such that adjacent sensor elements are attached to different sides of said frame rails.

4. A low profile acoustic sensor away, comprising:
a plurality of longitudinally extending sensor strips, each of said strips having at least one sensor element included thereon, wherein said at least one sensor element is configured so as to respond to acoustic wavelengths in the frequency range of interest and to inhibit response to compressional wavelengths in the frequency range of interest so as to mechanically filter acoustic signals detected by the sensor array,
wherein each of said plurality of longitudinally extending sensor strips comprise:
a plurality of longitudinally spaced apart separate sensor elements included thereon;
a sensor frame having a length and at least one longitudinally extending frame rail;
wherein each of said plurality of acoustic sensor elements attached to said at least one frame rail, wherein each of said acoustic sensor elements is sized and configured to extend transversely from said frame rail, and wherein each of said sensor elements have a pliable configuration; and
a plurality of separate electrical signal paths, at least one for each of said sensor elements, said electrical signal paths defining a signal path from a respective one of each of said sensor elements to a desired end electrical termination point.

5. An acoustic sensor array according to claim 4, wherein each of said strips is a unitary body along a major portion of its length, and wherein each of said sensor elements laterally extends from one of said at least one frame rails such that said sensor elements in each strip are linearly aligned along the length of said strip.

6. An acoustic sensor array according to claim 4, said frame rails and said sensor elements have an upper surface, and wherein said upper surface of said frame rails and said sensor elements have a substantially constant and flat contour when viewed from the side when positioned on a subject.

7. An acoustic sensor array according to claim 6, said strip further comprising a longitudinally extending neck portion having opposing first and second ends, wherein said sensor element frame is attached to said neck portion first end and said termination point is an electrical connector positioned adjacent said neck second end.

8. An acoustic array according to claim 7, wherein said frame rails comprise a first PVDF layer, a second intermediate core layer, and a third PVDF layer, wherein said first and third PVDF layers sandwich said second core layer.

9. An acoustic array according to claim 8, wherein said electrical signal path is defined by two spatially separate opposing electrical traces formed onto said first and third PVDF layers, said separate electrical traces including a first electrical linear trace with a first rectangular sensor element region and a corresponding second linear trace with a second rectangular sensor element region, wherein said first electrical linear trace and first rectangular region disposed onto said first PVDF layer and said second electrical linear trace and second rectangular region disposed onto said third PVDF layers.

10. An acoustic sensor according to claim 9, wherein said operational frequency range includes at least the frequency range of about 100 to 1000 hertz.

11. An acoustic sensor according to claim 10, wherein said sensor generates a response during flexure which has an output substantially equal to the voltage differential between said first and second voltages.

12. An acoustic sensor array according to claim 4, wherein said sensor array further comprises a plurality of discrete masses, one positioned on each of said sensor elements.

13. An acoustic sensor array according to claim 4, wherein each of said sensor elements comprises a first PVDF layer overlying and contacting a second flexible core layer and a third PVDF layer opposing said first layer and contacting said core layer.

14. An acoustic sensor array according to claim 13, wherein said electrical signal paths are formed by a conductive pattern formed onto said first and second PVDF film layers.

15. An acoustic array according to claim 14, wherein said frame rails and said sensor elements comprise the same multi-layer materials in the same thicknesses.

16. An acoustic array according to claim 13, wherein said first layer PVDF is selectively actively polarized about portions of sensor elements and substantially non-actively polarized about said frame sides to provide increased signal isolation.

17. An acoustic array according to claim 16, wherein said plurality of sensor elements is six.

18. An acoustic array according to claim 13, wherein said core layer comprises neoprene.

19. An acoustic array according to claim 4, wherein said plurality of strip arrays is four.

20. An acoustic strip sensor array, comprising:
a sensor frame having a frame length and including at least one longitudinally extending rail;
a plurality of acoustic sensor elements attached to said rail, wherein said acoustic sensor element is sized and configured to extend a transverse distance away from said rail, said sensor element having a pliable configuration; and
first and second opposing spatially separate electrical signal paths for each of said sensor elements, wherein in response to flexure of said sensor elements, said first and second electrical signal paths are configured to provide opposing polarities defining a differential signal output for a respective one of each of said sensor elements, wherein said sensor array has an operational frequency range which includes the frequency range of about 100 to 1000 hertz.

21. An acoustic strip sensor array according to claim 20, wherein said acoustic strip sensor array has a substantially planar profile along said frame and said sensor elements when viewed form the side.

22. An acoustic strip sensor array according to claim 20, wherein said frame and said sensor elements are sized and configured to flex in response to movement associated with shear waves and to inhibit element flexure associated with long compression waves in the acoustic frequency range of interest.

23. An acoustic strip sensor array according to claim 20, wherein when engaged on the surface of a patient, said sensor elements flex in response to acoustic waves having a propagation velocity of less than about 100 m/s, and wherein said sensor elements are sized and configured to inhibit flexure in response to acoustic waves having a propagation velocity longer than about 300 n/s.

24. An acoustic strip sensor array according to claim 20, wherein said sensor elements and said frame elements comprise a resilient core layer and opposing first and second outer layers comprise PDVF.

25. An acoustic strip sensor array according to claim 24, wherein said first and second electrical signal paths are positioned to be on internal surfaces of said first and second outer layers, positioned with respect so said core to face the other across the width of said core, such that, during operation and engagement with a patient, flexure of said sensor generates a first and second response voltage corresponding to a respective one of said first and second electrical signal paths, wherein said sensor array signal output for each sensor element is defined by the voltage differential between said first and second voltages.

26. An acoustic strip sensor array according to claim 25, further comprising a plurality of discrete masses, at least one each attached to each of said plurality of acoustic sensor elements.

27. An acoustic strip sensor array according to claim 24, wherein said core layer has a first relative permittivity and said first and second pliable material layers have a second relative permittivity such that said first relative permittivity is less than said second relative permittivity.

28. An acoustic strip sensor array according to claim 24, wherein said strip sensor array is configured such that said first and second electrical signal paths are defined by traces formed on the internal facing surfaces of said first and second outer layers, and wherein said signal paths include a ground plane defined by an electrical trace formed on the externally facing surfaces of said first and second outer layers.

29. An acoustic strip sensor array according to claim 20, wherein said frame and said acoustic sensor elements define a unitary body comprising spaced apart frame rails with the sensor elements disposed therebetween, wherein each of said sensor elements is attached to a selected one of said frame rails, wherein the unitary body comprises an elongate neck portion with a first width that merges into the frame rails that span a second larger width, and wherein a respective electrical transmission path for a sensor element laterally extends outward from a corresponding acoustic sensor element then turns to extend longitudinally about the one longitudinally extending rail, then laterally turns inward a distance and extends longitudinally along the neck portion.

30. An acoustic sensor array, comprising:
a plurality of unitary acoustic sensor elements;
a plurality of transmission lines having opposing first and second ends and defining a length therebetween, a respective one transmission line for each of said plurality of unitary acoustic sensors, said transmission line first end individually attached to a respective one of said acoustic sensor elements; and
wherein each of said transmission lines is configured with a series of undulations along its length.

31. An acoustic array according to claim 30, further comprising a carrier member releasably attached to each of said sensor elements.

32. An acoustic array according to claim 30, further comprising a plurality of discrete masses, at least one attached to each of said plurality of sensors.

33. An acoustic array according to claim 32, wherein said discrete mass includes a reflective surface thereon.

34. An acoustic sensor array according to claim 30, wherein said array is configured such that each of said unitary sensor elements are structurally separate and discrete from the others along the sensor element and transmission line.

35. An acoustic sensor array according to claim 34, wherein said undulations are formed onto said transmission lines as a series of continuously repeating pleated segments.

36. An acoustic sensor array according to claim 34, further comprising a connector configured to receive a portion of each of said transmission line second ends therein.

37. An acoustic sensor array according to claim 34, wherein said sensor element includes a piezoelectrically active film configured to define two spatially separated opposing electrode surfaces with opposing polarities, and wherein during operation said opposing electrode surfaces produce first and second voltages, respectively, and each of said sensor elements is configured to generate a signal output defined by the voltage differential between said first and second voltages in response to flexure of said electrode surfaces.

38. An acoustic sensor array according to claim 30, wherein said plurality of elements comprises three linearly arranged substantially flat elements.

39. An acoustic sensor array, comprising:
a plurality of unitary acoustic sensor elements;
a plurality of transmission lines having opposing first and second ends an defining a length therebetween, a respective one transmission line for each of said plurality of unitary acoustic sensors, said transmission line first end individually attached to a respective one of said acoustic sensor elements; and wherein each of said transmission lines is configured with a series of undulations along its length wherein said sensor element comprises:

a resilient core layer comprising a low permittivity material having a core thickness;

a first pliable material layer sized and configured to sandwich and overlay said core layer, said first material layer comprising a piezoelectrically active material having opposing first and second major surfaces;

first and second electrical traces disposed on said first major surface of said first pliable material layer, said first and second electrical traces defining a spatially separate first and second electrode, wherein in position over said core, said first electrode has an opposite polarity relative to said second electrode; and an exterior conductive shield layer sized and configured to overlay said second major surface of said first material layer;

and wherein said transmission line defines a linear transmission line attached to said sensor element, said linear transmission line including first and second ends and extending a linear length therebetween, comprising;

a first pliable material layer extending from said first end to said second end of said linear transmission line having opposing first and second major surfaces, said first pliable material layer comprising a piezoelectrically active material;

first, second, and third electrical traces disposed on said first pliable material layer in electrical communication with said sensor element first material layer electrical traces, said first and second electrical traces disposed on said first major surface and said third electrical trace disposed on said second major surface;

first and second layers of a non-conducting film configured and sized to respectively overlay a major portion of said first and second major surfaces of said first pliable material layer;

a first linear outer layer conductive strip configured and sized to overlay a major portion of first non-conducting film layer opposite said first major surface of said first pliable material layer; and a second linear outer layer conductive strip configured and sized to overlay a major portion of said second non-conducting film layer opposite said second major surface of said first pliable material layer;

wherein said first pliable material layer of said transmission line and said first pliable material layer of said sensor element is a unitary layer, and wherein said third electrical trace of said first pliable material layer provides an electrical ground operably associated with said first and second conductive outer layers of said sensor.

40. An acoustic sensor according to claim 39, wherein said transmission line is configured with a series of undulations along its length.

41. An acoustic sensor according to claim 39, further comprising at least one discrete mass attached to said sensor element.

42. An acoustic sensor array, comprising:

a plurality of compliant sensor elements having first and second outer surfaces, said first outer surface configured to attach to a subject such that it is substantially conformal to the subject; and a carrier member releasably attached to said second outer surface of each of said plurality of sensor elements to hold said plurality of sensors in alignment during positioning on a subject;

wherein said carrier member is disengaged from said sensor elements after said sensor elements are attached to a desired location on the subject without causing said sensor elements to move from the desired location.

43. An acoustic sensor array according to claim 42, wherein said carrier member includes an externally accessible tab.

44. An acoustic sensor array according to claim 42, further comprising a plurality of discrete masses, at least one attached to each of said sensor elements.

45. An acoustic sensor array according to claim 44, wherein a predetermined number of said discrete masses includes a reflective surface.

46. An acoustic sensor array according to claim 42, further comprising a plurality of discrete stiffeners, at least one attached to each of said sensor elements.

47. An acoustic sensor array according to claim 46, wherein a predetermined number of said stiffeners includes a reflective surface.

48. An acoustic sensor array according to claim 42, further comprising a plurality of transmission lines and a connector, wherein each of said sensor elements are operably associated with a respective one of said transmission lines, and wherein each of said transmission lines are connected to said connector.

49. An acoustic sensor array according to claim 48, wherein each of said transmission lines are configured with a series of undulations along its length.

50. An acoustic sensor array according to claim 42, said wherein said sensor elements comprise opposing first and second electrodes having opposing polarities and a center core having a thickness disposed therebetween, wherein said electrodes are defined by a piezoelectrically active film and wherein said core thickness defines the separation distance between said first and second electrodes.

51. A method of forming an acoustic sensor said acoustic sensor having a sensor pad region and a transmission line, comprising the steps of:

configuring a first unitary layer of PVDF film having first and second opposing major surfaces with a laterally extending region having a first width and a longitudinally extending region having a second width;

forming sensor element electrical traces onto the first major surfaces of the PVDF layer, the sensor electrical traces are arranged as a rectangular shape onto the lateral region of the PVDF layer such that the lateral region defines first and second separate electrode regions with opposing polarity;

forming electrical traces onto the longitudinally extending region of the first and second major surfaces of the PVDF layer to define three electrical paths, wherein the first and second paths are formed on one major surface to provide the electrical signal path for the first and second electrode regions, and wherein the third path is formed on the opposing major surface of the PVDF layer and is configured with a primary finger portion;

inserting a resilient core onto a surface of one of the electrode regions;

positioning non-conducting film to overlay substantially the entire length of the longitudinally extending region of the PVDF layer;

positioning a first electric shield material to overlay the non-conducting film on the side opposing the first major surface of the PVDF film, wherein the first electrical shield includes a conductive secondary finger portion;

providing a second electric shield layer configured and sized to mirror the PVDF film shape, to overlay the second major surface of the PVDF film in the laterally extending electrode region and to overlay and contact the non-conducting film in the longitudinally extending region;

folding the laterally extending region of the PVDF film over the core such that the first and second electrode regions are positioned opposing the other with the core is positioned intermediate thereof; and folding the primary finger of the ground strip to overlay the first major surface, wherein electrical contact between the first and second conductive shield material at the termination end thereby provides a substantially continuous electric shield for the sensor.

52. A method according to claim 51, further comprising the step of forming undulations along a portion of the length of said longitudinally extending region.

53. A low profile acoustic sensor array, comprising:

a plurality of longitudinally extending sensor strips, each of said strips having at least one sensor element included thereon, wherein said at least one sensor element is configured so as to respond to acoustic wavelengths in the frequency range of interest and to inhibit response to compressional wavelengths in the frequency range of interest so as to mechanically filter acoustic signals detected by the at least one sensor element, wherein said at least one sensor element comprises:

a resilient core layer comprising a low permittivity material having a core thickness;

a first pliable material layer overlaying and contacting said core layer, said first material layer comprising a piezoelectrically active material, said first pliable layer having opposing internal and external surfaces;

a second pliable material layer overlaying and contacting said core layer opposing said first pliable material layer, said second pliable layer comprising a piezoelectrically active material and having opposing internal and external surfaces;

a first electrical trace disposed on said first pliable material layer inner surface; and a second electrical trace disposed on said second pliable material layer inner surface such that said first and second electrical traces face each other across said core layer, wherein during operation and in response to flexure of said sensor element, said first and second electrical traces generate respective first and second voltages, and wherein said first and second voltages have opposing polarity.

54. An acoustic sensor array according to claim 53, wherein said core layer comprises neoprene.

55. An acoustic sensor array according to claim 54, wherein said core layer has a first relative permittivity and said first and second pliable material layers have a second relative permittivity, such that said first relative permittivity is at less than said second relative permittivity.

56. An acoustic sensor array according to claim 53, wherein said core thickness defines the separation distance between said first and second pliable layers.

57. An acoustic sensor array according to claim 56, wherein said first and second pliable material layers are formed from PVDF.

58. An acoustic sensor array according to claim 57, wherein said core layer has a thickness of about 30 microns, and wherein said first and second pliable layers have a thickness of about 600 microns.

* * * * *

UNITED STATES PATENT AND TRADEMARK OFFICE
CERTIFICATE OF CORRECTION

PATENT NO. : 7,037,268 B1
APPLICATION NO. : 09/914682
DATED : May 2, 2006
INVENTOR(S) : Sleva et al.

It is certified that error appears in the above-identified patent and that said Letters Patent is hereby corrected as shown below:

Column 6,
Line 8, after "and the third electrical trace of the first pliable" please insert
-- material layer provides an electrical ground operably associated with the first and second conductive outer layers of the sensor. In a preferred embodiment, the acoustic sensor transmission line is configured with a series of undulations along its length.

Yet another aspect of the present invention is an acoustic sensor array, comprising a plurality of sensor elements having first and second outer surfaces. The first outer surface is configured to attached to a subject. The sensor array also includes a carrier member release-ably attached to the second outer surface of each of the plurality of sensor elements to hold the plurality of sensors in alignment. In operation, the carrier member is disengaged from the sensor elements after the sensor elements are attached to the subject. In one embodiment, the sensor elements are a set of discrete (structurally separate) sensor elements and the carrier member maintains positional alignment of the sensor elements for easier positioning onto a subject. Advantageously, the carrier member can also be used for other sensor configurations, and is particularly useful for resilient or compact flexural element configurations (such as the strip sensor embodiment described herein).

An additional aspect of the present invention is directed to a method of minimizing the mechanical interference between one or more or adjacent sensors and the end of the transmission line. For example, the method can minimize interference between adjacent sensors and system or environment mechanical forces which potentially can be input to the sensor by mechanically isolating flexure responsive acoustic sensor elements in arrays having a plurality of sensor elements. The method comprises the step of forming a series of undulations in a electrical transmission path to provide mechanical damping therealong. Preferably, the acoustic sensor array includes a plurality of sensor elements and a and a separate electrical transmission path for each of said sensor elements and the method further comprises the step of forming the sensor array such that the plurality of sensor elements and associated sensor electrical transmission paths are physically separate units.

Another aspect of the present invention is a method of forming an acoustic --

Page 1 of 2

UNITED STATES PATENT AND TRADEMARK OFFICE
CERTIFICATE OF CORRECTION

PATENT NO.       : 7,037,268 B1
APPLICATION NO.  : 09/914682
DATED            : May 2, 2006
INVENTOR(S)      : Sleva et al.

It is certified that error appears in the above-identified patent and that said Letters Patent is hereby corrected as shown below:

Column 30,
Line 67 should read -- second ends and defining a length therebetween, a --

Signed and Sealed this

Tenth Day of October, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,037,268 B1 |
| APPLICATION NO. | : 09/914682 |
| DATED | : May 2, 2006 |
| INVENTOR(S) | : Sleva et al. |

It is certified that error appears in the above-identified patent and that said Letters Patent is hereby corrected as shown below:

Column 6,
Line 8, after "and the third electrical trace of the first pliable" please insert
-- material layer provides an electrical ground operably associated with the first and second conductive outer layers of the sensor. In a preferred embodiment, the acoustic sensor transmission line is configured with a series of undulations along its length.

Yet another aspect of the present invention is an acoustic sensor array, comprising a plurality of sensor elements having first and second outer surfaces. The first outer surface is configured to attach to a subject. The sensor array also includes a carrier member release-ably attached to the second outer surface of each of the plurality of sensor elements to hold the plurality of sensors in alignment. In operation, the carrier member is disengaged from the sensor elements after the sensor elements are attached to the subject. In one embodiment, the sensor elements are a set of discrete (structurally separate) sensor elements and the carrier member maintains positional alignment of the sensor elements for easier positioning onto a subject. Advantageously, the carrier member can also be used for other sensor configurations, and is particularly useful for resilient or compact flexural element configurations (such as the strip sensor embodiment described herein).

An additional aspect of the present invention is directed to a method of minimizing the mechanical interference between one or more or adjacent sensors and the end of the transmission line. For example, the method can minimize interference between adjacent sensors and system or environment mechanical forces which potentially can be input to the sensor by mechanically isolating flexure responsive acoustic sensor elements in arrays having a plurality of sensor elements. The method comprises the step of forming a series of undulations in a electrical transmission path to provide mechanical damping therealong. Preferably, the acoustic sensor array includes a plurality of sensor elements and a separate electrical transmission path for each of said sensor elements and the method further comprises the step of forming the sensor array such that the plurality of sensor elements and associated sensor electrical transmission paths are physically separate units.

Another aspect of the present invention is a method of forming an acoustic --

UNITED STATES PATENT AND TRADEMARK OFFICE
CERTIFICATE OF CORRECTION

PATENT NO. : 7,037,268 B1
APPLICATION NO. : 09/914682
DATED : May 2, 2006
INVENTOR(S) : Sleva et al.

It is certified that error appears in the above-identified patent and that said Letters Patent is hereby corrected as shown below:

Column 30,
Line 67 should read -- second ends and defining a length therebetween, a --

This certificate supersedes Certificate of Correction issued October 10, 2006.

Signed and Sealed this

Sixth Day of February, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,037,268 B1 | Page 1 of 1 |
| APPLICATION NO. | : 09/914682 | |
| DATED | : May 2, 2006 | |
| INVENTOR(S) | : Sleva et al. | |

It is certified that error appears in the above-identified patent and that said Letters Patent is hereby corrected as shown below:

Title Page

Section [54] and Column 1, lines 1-3 should read:
--LOW PROFILE ACOUSTIC SENSOR ARRAY AND SENSORS WITH PLEATED TRANSMISSIONS LINES AND RELATED METHODS--

Signed and Sealed this

Tenth Day of April, 2007

JON W. DUDAS
*Director of the United States Patent and Trademark Office*

UNITED STATES PATENT AND TRADEMARK OFFICE
CERTIFICATE OF CORRECTION

PATENT NO. : 7,037,268 B1
APPLICATION NO. : 09/914682
DATED : May 2, 2006
INVENTOR(S) : Sleva et al.

It is certified that error appears in the above-identified patent and that said Letters Patent is hereby corrected as shown below:

<u>Title Page</u>

Section [54] and Column 1, lines 1-3 should read:
--LOW PROFILE ACOUSTIC SENSOR ARRAY AND SENSORS WITH PLEATED TRANSMISSION LINES AND RELATED METHODS--

This certificate supersedes Certificate of Correction issued April 10, 2007.

Signed and Sealed this

Third Day of July, 2007

JON W. DUDAS
*Director of the United States Patent and Trademark Office*